US012791568B2

(12) United States Patent
Svanborg et al.

(10) Patent No.: US 12,791,568 B2
(45) Date of Patent: Nov. 10, 2026

(54) TREATMENT AND DIAGNOSIS OF CHRONIC INFLAMMATORY CONDITIONS IN THE LOWER URINARY TRACT

(71) Applicant: SELECTIMMUNE PHARMA AB, Lund (SE)

(72) Inventors: Catharina Svanborg, Lund (SE); Björn Wullt, Lund (SE); Daniel Butler, Lund (SE); Ines Ambite, Lund (SE)

(73) Assignee: SELECTIMMUNE PHARMA AB, Lund (SE)

( * ) Notice: Subject to any disclaimer, the term of this patent is extended or adjusted under 35 U.S.C. 154(b) by 1316 days.

(21) Appl. No.: 17/617,204

(22) PCT Filed: Jun. 8, 2020

(86) PCT No.: PCT/EP2020/065856

§ 371 (c)(1),
(2) Date: Dec. 7, 2021

(87) PCT Pub. No.: WO2020/245464

PCT Pub. Date: Dec. 10, 2020

(65) Prior Publication Data

US 2022/0252625 A1 Aug. 11, 2022

(30) Foreign Application Priority Data

Jun. 7, 2019 (SE) .................................. 1950680-7
Aug. 29, 2019 (GB) ...................................... 1912423
Jan. 30, 2020 (GB) ...................................... 2001320

(51) Int. Cl.
*A61K 38/20* (2006.01)
*A61P 29/00* (2006.01)
*G01N 33/94* (2006.01)

(52) U.S. Cl.
CPC ..... *G01N 33/9406* (2013.01); *A61K 38/2006* (2013.01); *A61P 29/00* (2018.01); *G01N 2333/545* (2013.01); *G01N 2800/34* (2013.01); *G01N 2800/361* (2013.01); *G01N 2800/364* (2013.01)

(58) Field of Classification Search
None
See application file for complete search history.

(56) References Cited

U.S. PATENT DOCUMENTS

| | | | |
|---|---|---|---|
| 2001/0053764 | A1 | 12/2001 | Sims et al. |
| 2005/0152905 | A1 | 7/2005 | Omoigui |
| 2006/0128794 | A1 | 6/2006 | Sandage, Jr. et al. |
| 2011/0160157 | A1 | 6/2011 | Wang et al. |
| 2018/0031253 | A1 | 2/2018 | McCune et al. |

FOREIGN PATENT DOCUMENTS

| | | | |
|---|---|---|---|
| DE | 102011083595 | A1 | 3/2013 |
| EP | 1811303 | B1 | 7/2007 |
| EP | 1880719 | A2 | 1/2008 |
| WO | 03/014309 | A2 | 2/2003 |
| WO | 2010/075287 | A2 | 7/2010 |
| WO | 2010/111787 | A1 | 10/2010 |
| WO | 2012/078101 | A1 | 6/2012 |
| WO | 2012/122985 | A1 | 9/2012 |
| WO | 2016/110818 | A2 | 7/2016 |
| WO | 2020/245464 | A1 | 12/2020 |

OTHER PUBLICATIONS

Atmani et al., "P1686 Neuro-Glial Modulation Associated With Pelvic Organs Cross-Sensitization: Effect on Chronic Visceral Nociception", United European Gastroenterology Journal 6 (8S), 2018, A683-A684, vol. 6, No. 8.
Swedish Search Report from Swedish Patent Application No. 1950680-7, dated Nov. 27, 2019; 3 pgs.
International Search Report and Written Opinion from International Application No. PCT/EP2020/065856, dated Nov. 4, 2020; 19 pgs.
Alexander et al., "Elevated Levels of Proinflammatory Cytokines in the Semen of Patients with Chronic Prostatitis/Chronic Pelvic Pain Syndrome," Urology, 1998, pp. 744-749, vol. 52, No. 5.
Jiang et al., "Increased Pro-Inflammatory Cytokines, C-Reactive Protein and Nerve Growth Factor Expressions in Serum of Patients with Interstitial Cystitis/Bladder Pain Syndrome," PLOS One, 2013, e76779, pp. 1-6, vol. 8, No. 10.
Michaud et al., "Decreased concentrations of soluble interleukin-1 receptor accessory protein levels in the peritoneal fluid of women with endometriosis," Journal of Reproductive Immunology, 2011, pp. 68-73, vol. 92.
Nadler et al., "IL-1β and TNF-α in Prostatic Secretions Are Indicators in the Evaluation of Men With Chronic Prostatitis," The Journal of Urology, 2000, pp. 214-218, vol. 164.
Srivastava et al., "Associations between IL-1RA polymorphisms and small intestinal bacterial overgrowth among patients with irritable bowel syndrome from India," Neurogastroenterology and Motility, 2014, pp. 1408-1416, vol. 26, No. 10.
Tudrej et al., "Role of NLRP3 inflammasome in the development of bladder pain syndrome interstitial cystitis," Therapeutic Advances in Urology, 2019, pp. 1-10, vol. 11.
Zhang et al., "Decreased levels of peritoneal interleukin-1 receptor antagonist in patients with endometriosis and disease-related dysmenorrhea," Fertility and Sterility, 2007, pp. 594-599, vol. 88, No. 3.

*Primary Examiner* — Michael D Pak
(74) *Attorney, Agent, or Firm* — Polsinelli PC

(57) ABSTRACT

A method for treating chronic inflammatory conditions in the lower urinary tract, the method comprising administering to a patient in need thereof, an effective amount of a reagent selected from the group consisting of IL-1β inhibitors and MMP inhibitors, or proteins selected from ASC or NLRP-3 is provided. Diagnostic methods are also described and claimed. The present disclosure further relates to an IL-1 inhibitor for use in a method of treating, alleviating or reducing pain and pain related symptoms of chronic pelvic pain syndrome. The IL-1 inhibitor may be an IL-1 receptor antagonist. The IL-1 inhibitor may be anakinra. The chronic pelvic pain syndrome may be a urological pain syndrome, a gynecological pain syndrome of the external genitalia, an internal pelvic pain syndrome and a gastrointestinal pelvic pain syndrome.

18 Claims, 8 Drawing Sheets

Fig. 7a

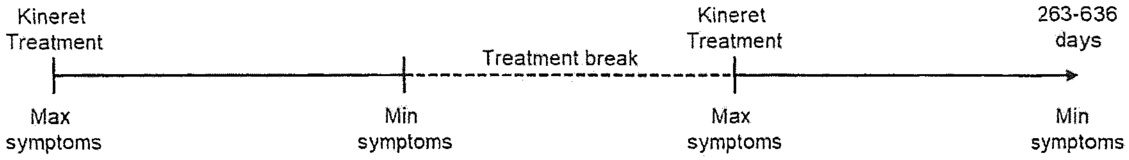

Fig. 7b

| ID | Age (years) | M/F | CIC/ Cath | CPPS/ main subtype | Symptom duration (year/s) | Cystoscopy inflammation Yes/No | Histology | Concomitan diseases, Comment |
|---|---|---|---|---|---|---|---|---|
| PP | 61 | M | CIC | BPS | 2 | Yes | Inflammation | Partial paraparesis, neurogenic bladder diorder, kidney stone |
| AH | 67 | M | -- | BPS | > 10 | Yes | Inflammation | Benign prostate hyperplasia |
| EJ | 67 | F | --- | BPS | > 10 | Yes | ND | Heathy otherwise |
| AJ | 77 | F | Cath | BPS | 2 | Yes | Inflammation | Small contracted bladder, previous irradiation due to |
| CL | 78 | F | --- | BPS | year | Yes | Inflammation | Gynoecological cancer, chronic obstructive pulmonary disease |
| MP | 39 | F | --- | BPS | 1 | No | ND | Healhy otherwise |
| SS | 70 | F | --- | BPS | > 10 | No | ND | Mb Dercum |
| HL | 70 | M | --- | PPS/BPS | < 1 | No | ND | Prostate pain / chronic pelvic pain |
| WL | 65 | M | --- | BPS | >10 | Yes | Cystitis Cystica | Unspecified intermittent fever, artralgia |
| MF | 47 | F | --- | BPS | >10 | No | Normal | Healthy otherwise |
| BS | 67 | M | --- | BPS | > 2 years | Yes | Pending | Healthy otherwise |

Fig. 7c

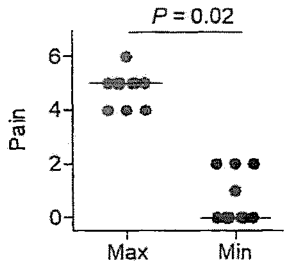

Fig. 7d

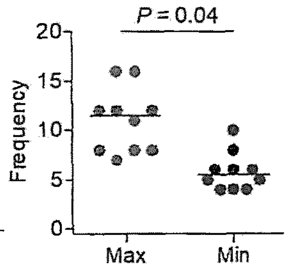

Fig. 7e

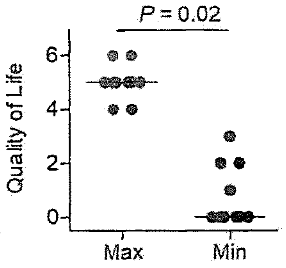

Fig. 7f

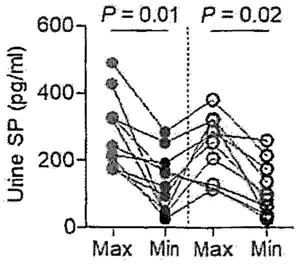

Fig. 8

A B

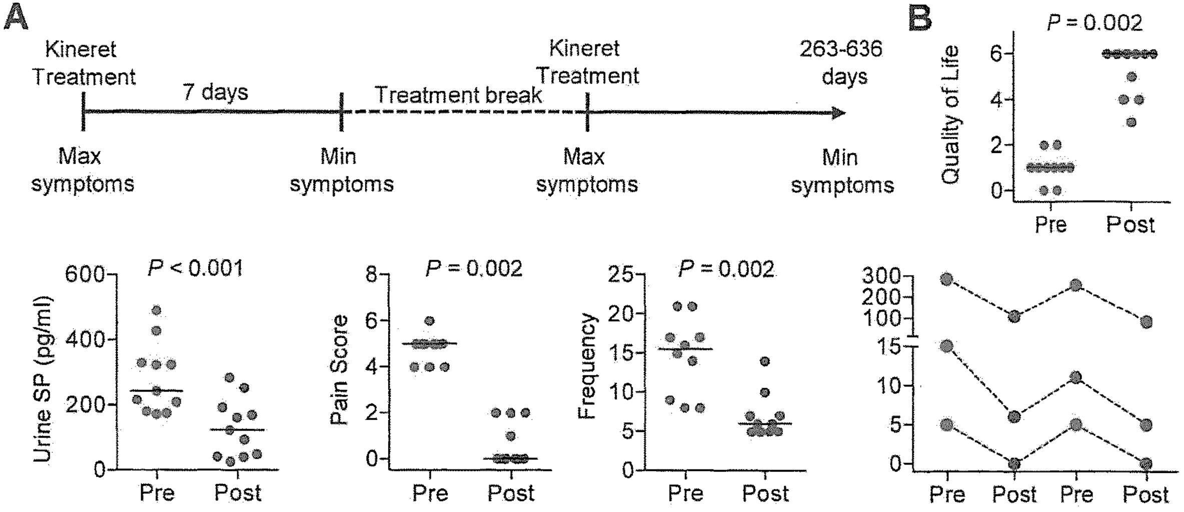

C

| ID | Age (years) | M/F | CIC/ Cath | CPPS-main/ subtype | Symptom duration (year/s) | Inflammation Cytoscopy/ Histology | Concomitan diseases, Comment | Response (Y/N) |
|---|---|---|---|---|---|---|---|---|
| *Bladder Pain Syndrome (with inflammation)* | | | | | | | | |
| AJ | 77 | F | Cath | BPS | 2 | +/+ | Small contracted bladder, previous irradiation due to gynoecological cancer, chronic obstructive pulmonary disease | CR |
| AH | 67 | M | -- | BPS | > 10 | +/+ | benign prostate hyperplasia | CR |
| PP | 61 | M | CIC | BPS | 2 | +/+ | Partial paraparesis, neurogenic bladder diorder, kidney stone | CR |
| EJ | 67 | F | -- | BPS | > 10 | +/nd | healhy otherwise | CR |
| BS | 67 | M | -- | BPS | > 2 years | +/+ | Otherwise healthy | PR |
| CL | 78 | F | -- | BPS | 1 | +/+ | | NR/PR |
| *Bladder Pain Syndrome (without inflammation)* | | | | | | | | |
| MF | 47 | F | -- | BPS | >10 | -/- | Otherwise healthy | CR |
| HL | 70 | M | -- | PPS/BPS | < 1 | -/nd | Prostate pain / chronic pelvic pain | CR |
| MP | 39 | F | -- | BPS | 1 | -/nd | Otherwise healthy | CR |
| SS | 70 | F | -- | BPS | > 10 | -/nd | Mb Dercum | CR |

D

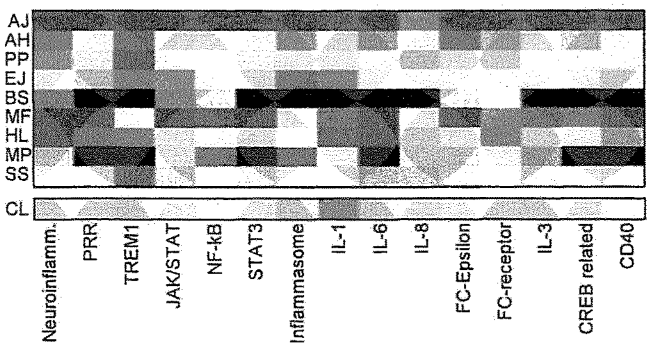

| Inflammatory genes | Mean FC |
|---|---|
| *CASP5* | -2.9 |
| *NAIP* | -2.0 |
| *MAPK14* | -2.0 |
| *NLRC4* | -2.0 |
| *MMP9* | -1.8 |
| *TLR5* | -1.7 |
| *CFLAR* | -1.5 |
| *TLR6* | -1.5 |
| *CREB5* | -1.5 |
| *IRAK3* | -1.4 |

Fig. 9

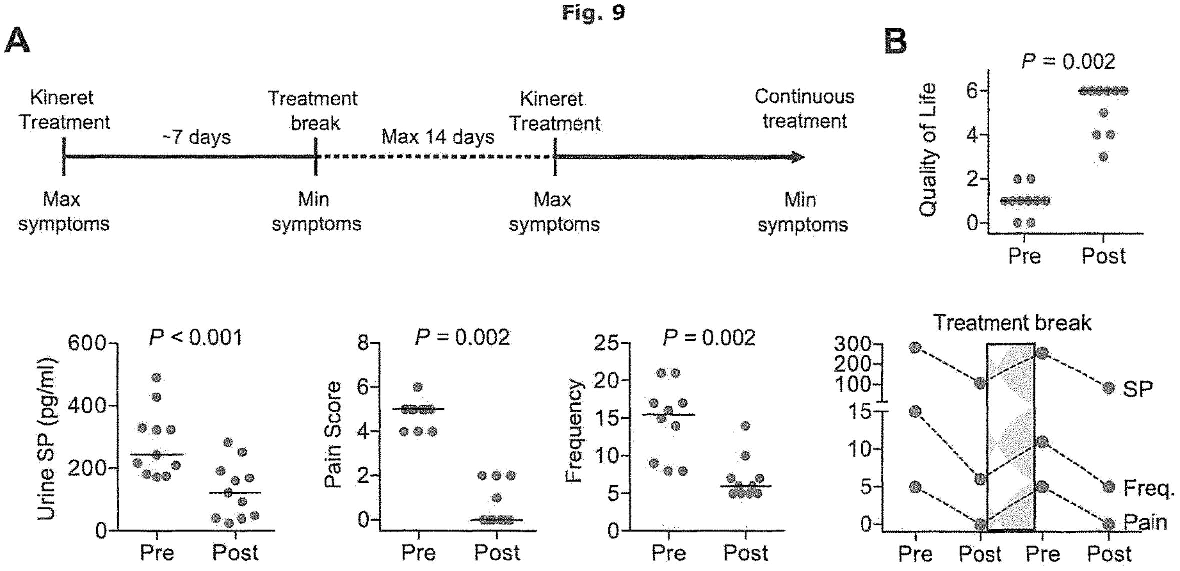

C

| ID | Short term effects | | | | Long term effects | |
|---|---|---|---|---|---|---|
| | Treatment response | Onset (hours) | Duration (Days) | Side effects | Observation time (Days) | Comment treatment |
| *Bladder Pain Syndrome with mucosal inflammation (Hunner's Ulcer)* | | | | | | |
| PI | Complete | 1-2 | 0.5 | Not reported | 512 | Ongoing, efficacy unchanged |
| PII | Complete | 4-6 | 1-2 | Transient neutropenia | 583 | Intermittent treatment ongoing, efficacy unchanged |
| PIII | Complete | 2 | 2-3 | Not reported | 706 | Ongoing, efficacy unchanged |
| PIV | Complete | 1-2 | 1-3 | Not reported | 482 | Treatment stopped due to no need after TURB on day 125 |
| PV | Partial | 4-6 | 1-2 | Not reported | 125 | Treatment stopped due to lack of effect on day 80 |
| PVI | Partial / no response | 2-4 | 3 | Not reported | 80 | Ongoing, efficacy unchanged |
| *Bladder pain Syndrome without mucosal inflammation* | | | | | | |
| PVII | Complete | 2 | 1 | Transient neutropenia | 299 | Ongoing, efficacy unchanged |
| PVIII | Complete | 1 | 8 | Headache | 28 | Patient stopped treatment on day 28, reason unknown |
| PIX | Partial / complete response | 2 | 2 | Not reported | 342 | Intermittent treatment ongoing, efficacy unchanged |
| PX | Complete | 2 | 3 | Local skin irritation | 420 | Ongoing, efficacy unchanged |
| **Median** | | **2** | **2.5** | | **482** | |

Fig. 10

A

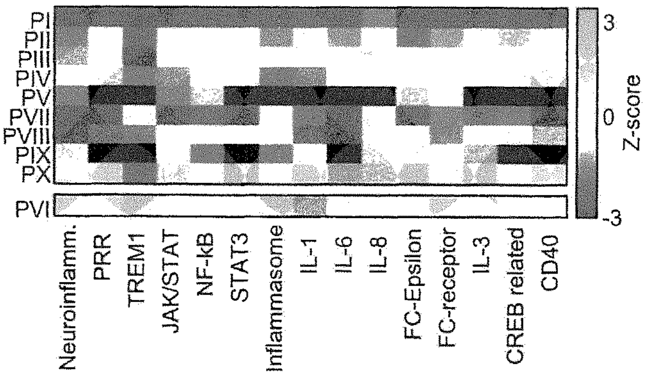

C

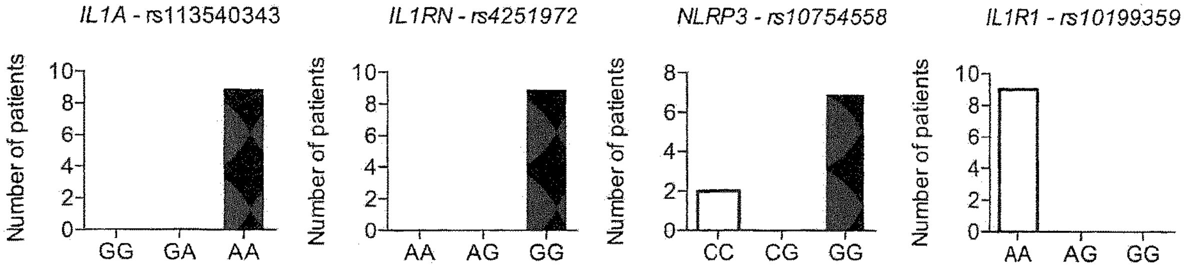

| Gene | SNP ID | Minor Allele | Patient | | | | | | | | | Allele Frequency % | |
|---|---|---|---|---|---|---|---|---|---|---|---|---|---|
| | | | I | II | III | IV | V | VII | VII | VIII | IX | Patients | Control |
| *IL1A* | rs113540343 | A | AA | AA | AA | AA | AA | AA | AA | AA | AA | 100% | 1% |
| *IL1RN* | rs4251972 | G | GG | GG | GG | GG | GG | GG | GG | GG | GG | 100% | 48% |
| *NLRP3* | rs10754558 | G | GG | GG | GG | GG | CC | GG | CC | GG | GG | 78% | 35% |
| *NLRP3* | rs147775898 | A | AG | AG | AG | AG | AG | AG | AG | AG | AG | 50% | 12% |
| *IL1RN* | rs2902452 | A | AC | AA | AA | AA | CC | CC | AC | AC | AC | 56% | 29% |
| *TACR1* | rs10168354 | G | AG | AA | AG | AG | AA | AG | AA | AA | AG | 28% | 55% |
| *TACR1* | rs768601 | C | AA | AA | AA | AA | AA | AA | AA | AC | AA | 6% | 32% |
| *IL1RN* | rs315931 | C | AA | AA | AA | AA | AC | AC | AC | AA | AA | 17% | 52% |
| *IL1R1* | rs6744454 | G | AA | AG | AG | AG | AA | AA | AG | AA | AA | 22% | 91% |
| *IL1R1* | rs10199359 | G | AA | AA | AA | AA | AA | AA | AA | AA | AA | 0% | 33% |

B

TREATMENT AND DIAGNOSIS OF CHRONIC INFLAMMATORY CONDITIONS IN THE LOWER URINARY TRACT

CROSS-REFERENCE TO RELATED APPLICATIONS

This application is a U.S. National Stage Application of International Application No. PCT/EP2020/065856, filed Jun. 8, 2020, which claims priority from SE Patent Application No. 1950680-7 filed on Jun. 7, 2019, GB Patent Application No. 1912423.9 filed on Aug. 29, 2019, and GB Patent Application No. 2001320.7 filed on Jan. 30, 2020, the entire contents of which are hereby incorporated by reference in their entirety.

FIELD OF THE INVENTION

The present invention relates to methods for treating chronic inflammatory conditions and chronic pain in the lower urinary tract, and to compositions for use in these therapies as well as diagnostic methods related thereto. In particular, it relates to an IL-1 inhibitor for use in a method of treating, alleviating or reducing pain and pain related symptoms of chronic pelvic pain syndrome.

BACKGROUND OF THE INVENTION

Chronic inflammatory conditions affect the urinary bladder and lower abdomen. Bladder pain is often caused by acute infections, but in certain individuals, chronic pain can endure in the absence of infection. As such, antibiotic therapy is not particularly useful in treatment of such conditions. Chronic cystitis (also referred to using terms such as interstitial cystitis (IC), bladder pain or bladder pain syndrome) may be accompanied by epithelial erosions or chronic pain without apparent gross inflammation. Chronic cystitis and bladder pain can be a solitary condition or be part of a more complex condition acting together with inflammatory processes in the prostate as well as the urethra (prostatitis and urethritis)—all included in Chronic Pelvic Pain Syndrome (CPPS).

Chronic Pelvic Pain (CPP) has been defined by the European Association of Urology (EAU Guidelines on Chronic Pelvic Pain, 2019) as chronic or persistent pain perceived in structures related to the pelvis of either men or women. It is often associated with negative cognitive, behavioural, sexual and emotional consequences as well as with symptoms suggestive of lower urinary tract, sexual, bowel, pelvic floor or gynaecological dysfunction. Perceived indicates that the patient and clinician, to the best of their ability from the history, examination and investigations (where appropriate) has localised the pain as being discerned in a specified anatomical pelvic area.

Chronic pelvic pain may be sub-divided into conditions with well-defined classical pathology (such as infection or cancer) and those with no obvious pathology. The EUA has proposed the term "specific disease-associated pelvic pain" is proposed for the former, and "chronic pelvic pain syndrome" (CPPS) for the latter.

Chronic pelvic pain syndrome is the occurrence of CPP when there is no proven infection or other obvious local pathology that may account for the pain. It is often associated with negative cognitive, behavioural, sexual or emotional consequences, as well as with symptoms suggestive of lower urinary tract, sexual, bowel or gynaecological dysfunction. Chronic Pelvic Pain Syndrome is a sub-division of CPP.

Pain perception in CPPS may be focused within a single organ, more than one pelvic organ and even associated with systemic symptoms such as chronic fatigue syndrome (CFS), fibromyalgia (FM) or Sjögren's syndrome. When the pain is localised to a single organ, some specialists may wish to consider using an end organ term such as e.g. bladder pain syndrome, prostate pain syndrome or urethral pain syndrome. The use of such a phrase with the terminology "syndrome" indicates that, although peripheral mechanisms may exist, CNS neuromodulation may be more important and systemic associations may occur. When the pain is localised to more than one organ site, the EAU recommends that the term CPPS should be used. Many, never sub-divide by anatomy and prefer to refer to patients with pain perceived within the pelvis, and no specific disease process, as suffering from CPPS, sub-divided by psychological and functional symptoms.

The treatment or management of CPPS includes conservative management as well as pharmacological management. Conservative management includes pain education, physiotherapy, acupuncture and psychological therapy. Pharmacological management involves the administration of anti-inflammatory drugs, α-blockers, antibiotic therapy (although CPPS is defined as chronic pelvic pain with no proven infection) and analgesics including morphine. Some patients have been shown to respond positively to different herbal medicine. In addition, e.g. anti-epileptics, muscle relaxants and botulinum toxin type A have been tested, but have shown inconclusive results. Many of the management pharmacological substances above give rise to problematic side effects.

The molecular basis of CPPS, cystitis and bladder pain has remained an enigma. Chronic bladder inflammation may cause debilitating pain, frequency and urgency of urination, sometimes accompanied by bladder ulcerations (interstitial cystitis), urethritis or prostatitis. Numerous therapeutic approaches have been tested but except for the use of antibiotics to treat infection and pain medications, therapeutic success has been limited and patients are often severely handicapped.

Specific treatments are currently lacking and the patients are offered pain management, often including opiates due to the severity of the clinical condition.

There is a need for treatments for CPPS and other chronic inflammatory conditions of the lower urinary tract.

SUMMARY OF THE INVENTION

The applicants have made the surprising discovery in experimental animal models that chronic inflammatory conditions and pain in the lower urinary tract respond dramatically to treatment that inhibited IL-1 activity. As such, the applicants have identified that such conditions can be treated with reagents such as interleukin-1 receptor antagonists and MMP inhibitors, as well as NK1R inhibitors. The effect of IL-1 inhibition was recently confirmed in a human clinical trial.

The applicants previously identified a new mechanism of IL-1β activation, involving the metalloproteinase MMP-7 in MMP-7 dependent processing and MMP-7 overexpression, in the bladder mucosa (WO2016/110818). The MMP-7 response may be explained by a direct effect of ASC and NLPR-3 on the MMP7 promoter, resulting in de-repression of Mmp7 expression in $Asc^{-/-}$ and $Nlrp3^{-/-}$ mice. As a consequence, the applicants found that treatment of Asc−/− mice by immunomodulation with a metalloproteinase inhibitor appeared to reduce IL-1β concentrations.

IL-1β is a potent pro-inflammatory cytokine that initiates and amplifies innate immune responses. IL-1β production increases in response to viral, bacterial, fungal and parasitic infections and IL-1β is essential for the defence against microbial attack. IL-1β responses may also be detrimental, however, and dysregulation of IL-1β has been observed in autoimmune and auto-inflammatory disorders, such as rheumatoid arthritis, multiple sclerosis, Crohn's disease or neuro-degenerative disorders.

The NLRP-3 inflammasome is activated by a number of microbial stimuli including LPS, MDP, bacterial RNA, poly(I:C) as well as ATP and bacterial pore-forming toxins. NLRP-3 activation stimulates the binding of ASC through homotypic pyrin domains and the caspase recruitment domain of ASC serves as an adaptor that binds NLRP-3 to pro-Caspase-1 to form the inflammasome. As seen previously (WO2016/110818), dysfunctional ASC or NLRP-3 proteins can have the downstream effect of elevating IL-1β levels and causing or worsening conditions involving IL-1β, such as chronic inflammatory conditions in the lower urinary tract.

Proteolytic cleavage by MMP-7 was previously identified as a new mechanism of IL-1β processing and evidence for IL-1β fragmentation by MMP-7 was obtained by direct cleavage of the purified components, in vitro. MMP-7 has metalloendopeptidase activity and is known to degrade collagen, proteoglycans, fibronectin, elastin and casein. MMP7 is activated following TNF-α or IL-1β stimulation of cells. It is commonly expressed in epithelial cells and has been shown to regulate the activity of defensins in the intestinal mucosa. IL-1β fragmentation by MMP-7 generates the active form of IL-1β, and therefore MMP inhibition is another route to treatment of chronic inflammatory conditions in the lower urinary tract.

The invention provides an agent that modulates the IL-1 pathway for use in the treatment of chronic inflammatory conditions in the lower urinary tract, such as chronic pelvic pain syndrome.

An agent that modulates the IL-1 pathway is an agent that modulates the activity at any gene, protein or other aspect of the pathway associated in IL-1 production or the binding of IL-1 to its receptor, or the effect of IL-1 binding to its receptor. It particularly refers to an agent that reduces the production, binding or effect of IL-1. For example, it may be an agent that reduces the production of IL-1. Or it may be an agent that affects the way IL-1 binds to its receptor, particularly reduces receptor binding. Or it may be an agent that interferes with the effect of IL-1 binding to its receptor, at any point in the pathway that follows. For example, the agent may affect the IL-1 pathway via interaction with IL1A, IL1B, IL1RN, IL1R1, NLRP3, PYCARD, MMP7, TAC1 and TACR1, or the products thereof, or the receptors of those products.

In particular, the invention provides one or more agents selected from an IL-1 inhibitor, an MMP inhibitor and an NK1 inhibitor, or a pharmaceutical composition comprising the one or more agents, for use in the treatment of chronic inflammatory conditions in the lower urinary tract. The invention further provides one or more agents selected from an IL-1 inhibitor, an MMP inhibitor and an NK1 inhibitor, or a pharmaceutical composition comprising the one or more agents, for use in the treatment of CPPS, particularly in treating, alleviating or reducing pain and pain related symptoms of CPPS.

An IL-1 inhibitor is any agent that inhibits or reduces IL-1 activity. For example, it may be a compound or composition that modulates the production of IL-1 or that interacts with IL-1 itself, or with the IL-1 receptor (IL-1R). In one embodiment, it is an IL-1R antagonist. IL-1R antagonists include, for example, small molecules such as anthraquinones, such as those described in U.S. Pat. No. 4,244,968 and including diacerein; proteins and peptides such as interleukin-1 receptor antagonists (IL-1 RA) including anakinra, as described in U.S. Pat. No. 5,075,222 and rilonacept; or pharmaceutically acceptable salts thereof, or prodrugs or functional fragments thereof; and compounds that function in the same way as those mentioned.

In one embodiment the IL-1 inhibitor may be chosen from anakinra, kanakinumab and diacerein. In a particular embodiment the IL-1 inhibitor is anakinra. The drug anakinra is an interleukin-1 receptor antagonist (r-metHuIL-1ra) produced in *Escherichia coli* cells. It is a recombinant and slightly modified version of the human interleukin-1 receptor antagonist protein which is a part of the feed-back loop balancing the effect of cytokine-induced inflammation. Anakinra is used in the treatment of Still's disease, and in combination with methotrexate in the treatment to manage symptoms of rheumatoid arthritis. Anakinra has also been suggested to be used in the treatment of acute cystitis, i.e. a bacterial infection of the bladder (WO 2016/110818).

In particular, the IL-1 inhibitor is an IL-1β inhibitor.

In a preferred embodiment, the interleukin-1 receptor antagonist is anakinra or a functional fragment or variant thereof.

An MMP inhibitor is a compound or composition that inhibits or reduces the activity of MMP. For example, it may be a compound or composition that modulates the production of MMP or that interacts with MMP itself, or with a region or receptor with which MMP interacts. In a particular embodiment, the MMP inhibitor is an MMP7 inhibitor. In one embodiment, it is an agent that modulates MMP, particularly MMP7, causing a reduction in IL-1, particularly Il-1β concentration or activation.

A wide range of MMP inhibitors are known as described for example Durrant et al. Chem. Biol. Drug Des 2011; 78; 191-198, the content of which is incorporated herein by reference. Particular examples include batimastat, periostat (doxycycline hyclate), marimastat, or salts or prodrugs thereof, but in particular batimastat.

NK1 inhibitors are agents that inhibit or reduce the activity of NK1. For example, an NK1 inhibitor may be a compound or composition that modulates the production of NK1 or that interacts with NK1 itself, or with the NK1 receptor (NK1R). In one embodiment, it is an NK1R inhibitor or antagonist. An example of NK1R antagonist is provided in WO2018/007920.

The agents may be used alone or in combination with each other or with other active agents.

The agents may be for use in the treatment of humans.

Chronic inflammatory conditions in the lower urinary tract include, for example, chronic cystitis, chronic pelvic pain syndrome and/or bladder-associated pelvic pain.

Chronic pelvic pain syndrome may be a urological pain syndrome, a gynecological pain syndrome of the external genitalia, an internal pelvic pain syndrome or a gastrointestinal pelvic pain syndrome. Specifically, the chronic pelvic pain syndrome may be prostate pain syndrome, bladder pain syndrome or urethral pain syndrome.

In particular, the pelvic pain excludes pelvic pain occurring in conjunction with acute infection (acute cystitis). In one embodiment, the invention relates to the treatment, alleviation and reduction of pain and pain-related symptoms in a subject suffering from chronic pelvic pain syndrome(s), i.e. chronic pelvic pain where no proven infection is present and where no other obvious local pathology is present. More specifically, the subject is a human. The treatment of CPPS according to the present disclosure aims at reducing the pain and increases the quality of life of the subject.

According to a further embodiment, said chronic pelvic pain syndrome is chosen from a urological pain syndrome, a gynecological pain syndrome of the external genitalia, an internal pelvic pain syndrome and a gastrointestinal pelvic pain syndrome.

According to another embodiment, said urological pain syndrome is chosen from prostate pain syndrome, bladder pain syndrome, scrotal pain syndrome, testicular pain syndrome, epididymal pain syndrome, penile pain syndrome, urethral pain syndrome and post-vasectomy scrotal pain syndrome.

Prostate pain syndrome (PPS) is defined by the EAU (*EAU Guidelines on Chronic Pelvic Pain,* 2019) as the occurrence of persistent or recurrent episodic pain (which is convincingly reproduced by prostate palpation). There is no proven infection or other obvious local pathology. Other terms commonly used for PPS, although not considered by the EUA to be appropriate, are chronic prostatitis and prostadynia.

Bladder pain syndrome (BPS) is defined by the EAU (*EAU Guidelines on Chronic Pelvic Pain,* 2019) as the occurrence of persistent or recurrent pain perceived in the urinary bladder region, accompanied by at least one other symptom, such as pain worsening with bladder filling and daytime and/or night-time urinary frequency. There is no proven infection or other obvious local pathology. Other terms that have been used, although no longer recommended, include interstitial cystitis, painful bladder syndrome, and PBS/IC or BPS/IC. In case of CPPS with Bladder Pain, or in BPS, several theories for the etiology have been suggested, including deficiency of glycosaminoglycans (GAGs) covering the urothelial surface, resulting in leaky urothelium infection, immunological etiology, activated mast cells, neural changes, and inflammation (Rourke et al., 2014). Intra-vesical treatment with e.g. solutions of dimethyl sulfoxide (DMSO), sodium hyaluronate (HA) or chondroitin sulfate (CS) are used for replenishing the GAG layer, with, however, various and mostly unreliable results. In one embodiment the agent is for the treatment of BPS.

Scrotal pain syndrome (SPS) is defined by the EAU (*EAU Guidelines on Chronic Pelvic Pain,* 2019) as the occurrence of persistent or recurrent episodic pain localised within the organs of the scrotum, and may be associated with symptoms suggestive of lower urinary tract or sexual dysfunction. There is no proven infection or other obvious local pathology. Scrotal pain syndrome is a generic term and is used when the site of the pain is not clearly testicular or epididymal.

Testicular pain syndrome (TPS) is defined by the EAU (*EAU Guidelines on Chronic Pelvic Pain,* 2019) as the occurrence of persistent or recurrent episodic pain perceived in the testes, and may be associated with symptoms suggestive of lower urinary tract or sexual dysfunction. There is no proven infection or other obvious local pathology. Other terms that have been used, although no longer recommended, include orchitis, orchialgia and orchiodynia.

Epididymal pain syndrome (EPS) is defined by the EAU (*EAU Guidelines on Chronic Pelvic Pain,* 2019) as the occurrence of persistent or recurrent episodic pain perceived in the epididymis, and may be associated with symptoms suggestive of lower urinary tract or sexual dysfunction. There is no proven infection or other obvious local pathology.

Penile pain syndrome (PPS) is defined by the EAU (*EAU Guidelines on Chronic Pelvic Pain,* 2019) as the occurrence of pain within the penis that is not primarily in the urethra, in the absence of proven infection or other obvious local pathology.

Urethral pain syndrome (UPS) is defined by the EAU (*EAU Guidelines on Chronic Pelvic Pain,* 2019) as the occurrence of chronic or recurrent episodic pain perceived in the urethra, in the absence of proven infection or other obvious local pathology. Urethral pain syndrome may occur in men and women.

Post-vasectomy scrotal pain syndrome is defined by the EAU (*EAU Guidelines on Chronic Pelvic Pain,* 2019) as a scrotal pain syndrome that follows vasectomy. Post-vasectomy pain may be as frequent as 1% following vasectomy, possibly more frequent. The mechanisms are poorly understood and for that reason it is considered a special form of scrotal pain syndrome.

According to another embodiment, said urological pain syndrome is chosen from prostate pain syndrome, bladder pain syndrome and urethral pain syndrome According to another embodiment, said bladder pain syndrome is bladder pain syndrome type 3c. Bladder pain syndrome (BPS) type 3c is a subtype of BPS that is combined with an incipient inflammatory lesion or with an inflammatory lesion (Hunner's ulceration) in the bladder.

Patients suffering from BPS type 3c have an increased risk of bladder contraction. Surgery with resection or coagulation of the lesion can result in pain reduction for longer periods, but if refractory to treatment surgical removal of the bladder (cystectomy) in combination with urinary diversion can be performed as a last treatment option.

Thus, a pharmaceutical treatment of BPS type 3c according to this disclosure has the advantage that surgical procedures can be avoided.

Furthermore, said bladder pain syndrome may be bladder pain syndrome without Hunner's ulcera (BPS).

According to another embodiment, said gynecological pain syndrome of the external genitalia is chosen from vulvar pain syndrome, generalized vulvar pain syndrome, localized vulvar pain syndrome, vestibular pain syndrome and clitoral pain syndrome.

Vulvar pain syndrome is defined by the EAU (*EAU Guidelines on Chronic Pelvic Pain,* 2019) as the occurrence of persistent or recurrent episodic vulvar pain. There is no proven infection or other local obvious pathology. Another term used for this condition is vulvodynia.

According to the EAU (*EAU Guidelines on Chronic Pelvic Pain,* 2019), generalized vulvar pain syndrome refers to a vulvar pain syndrome in which the pain/burning cannot be consistently and precisely localised by point-pressure mapping via probing with a cotton-tipped applicator or similar instrument. Rather, the pain is diffuse and affects all parts of the vulva. The vulvar vestibule (the part that lies between the labia minora into which the urethral meatus and vaginal introitus open) may be involved but the discomfort is not limited to the vestibule. Previous terms, although no longer recommended, included "dysesthetic vulvodynia" and "essential vulvodynia".

Localized vulvar pain syndrome is defined by the EAU (*EAU Guidelines on Chronic Pelvic Pain,* 2019) as referring to pain that can be consistently and precisely localised by point-pressure mapping to one or more portions of the vulva. Clinically, the pain usually occurs as a result of provocation (touch, pressure or friction). Localised vulvar pain syndrome can be sub-divided into vestibular pain syndrome and clitoral pain syndrome.

Vestibular pain syndrome is defined by the EAU (*EAU Guidelines on Chronic Pelvic Pain,* 2019) as referring to pain that can be localised by point-pressure mapping to the vestibule or is well perceived in the area of the vestibule.

Clitoral pain syndrome is defined by the EAU (*EAU Guidelines on Chronic Pelvic Pain,* 2019) as referring to pain that can be localised by point-pressure mapping to the clitoris or is well-perceived in the area of the clitoris.

According to another embodiment said internal pelvic pain syndrome is chosen from endometriosis associated pain syndrome, chronic pelvic pain syndrome with cyclical exacerbations and dysmenorrhea.

Endometriosis associated pain syndrome is defined by the EAU (*EAU Guidelines on Chronic Pelvic Pain,* 2019) as chronic or recurrent pelvic pain in patients with laparoscopically confirmed endometriosis, and the term is used when the symptoms persist despite adequate endometriosis treatment.

According to the EAU (*EAU Guidelines on Chronic Pelvic Pain,* 2019), chronic pelvic pain syndrome with cyclical exacerbations covers the non-gynaecological organ pain that frequently shows cyclical exacerbations (e.g., IBS or BPS) as well as pain similar to that associated with endometriosis/adenomyosis but where no pathology is identified. This condition is different from dysmenorrhoea, in which pain is only present with menstruation.

Dysmenorrhea is defined by the EAU (*EAU Guidelines on Chronic Pelvic Pain,* 2019) as pain with menstruation that is not associated with well-defined pathology. Dysmenorrhoea needs to be considered as a chronic pain syndrome if it is persistent and associated with negative cognitive, behavioural, sexual or emotional consequences.

According to another embodiment said gastrointestinal pelvic pain syndrome is chosen from irritable bowel syndrome, chronic anal pain syndrome and intermittent chronic anal pain syndrome.

Irritable bowel syndrome is defined by the EAU (*EAU Guidelines on Chronic Pelvic Pain,* 2019) as the occurrence of chronic or recurrent episodic pain perceived in the bowel, in the absence of proven infection or other obvious local pathology. Bowel dysfunction is frequent.

Chronic anal pain syndrome is defined by the EAU (*EAU Guidelines on Chronic Pelvic Pain,* 2019) as the occurrence of chronic or recurrent episodic pain perceived in the anus, in the absence of proven infection or other obvious local pathology.

Intermittent chronic anal pain syndrome is defined by the EAU (*EAU Guidelines on Chronic Pelvic Pain,* 2019) as referring to severe, brief, episodic pain that seems to arise in the rectum or anal canal and occurs at irregular intervals. This is unrelated to the need to or the process of defecation. It may be considered a sub-group of the chronic anal pain syndromes. Previous terms, although no longer recommended, include proctalgia fugax.

Treatment may mean the reduction or alleviation of pain. It may also or alternatively mean the reduction or alleviation of symptoms such as inflammation.

The invention further provides a method of treating chronic inflammatory conditions in the lower urinary tract, particularly CPPS, comprising the step of administering an agent that modulates the IL-1 pathway, such as one or more agents selected from an IL-1 inhibitor, an MMP inhibitor and an NK1 inhibitor, or a pharmaceutical composition comprising the one or more agents to a subject in need thereof.

In one embodiment, the present invention provides a method for treating chronic inflammatory conditions in the lower urinary tract comprising administering to a patient in need thereof an effective amount of a reagent selected from the group consisting of interleukin-1 receptor antagonists and MMP inhibitors.

The invention also provides a method of treating, alleviating or reducing pain and pain related symptoms of chronic pelvic pain syndrome in a subject, wherein the method comprises administering an agent that modulates the IL-1 pathway, particularly an IL-1 inhibitor to a subject in need thereof.

For administration to patients, the agent, reagent or protein is suitably administered in the form of a pharmaceutical composition, which further comprise a pharmaceutically acceptable carrier. Such compositions are known in the art.

Suitable pharmaceutical compositions will be in either solid or liquid form. They may be adapted for administration by any convenient route, such as parenteral, oral or topical administration or for administration by inhalation or insufflation. The pharmaceutical acceptable carrier may include diluents or excipients which are physiologically tolerable and compatible with the active ingredient.

Parenteral compositions are prepared for injection, for example either subcutaneously or intravenously. They may be liquid solutions or suspensions, or they may be in the form of a solid that is suitable for solution in, or suspension in, liquid prior to injection. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH-buffering agents, and the like.

In one embodiment, the agent, particularly an IL-1 inhibitor, is for administration by subcutaneous injection, intravenous injection, intramuscular injection, particularly by subcutaneous injection.

Oral formulations will be in the form of solids or liquids, and may be solutions, syrups, suspensions, tablets, pills, capsules, sustained-release formulations, or powders. Oral formulations include such normally employed excipients as, for example, pharmaceutical grades of mannitol, lactose, starch, magnesium stearate, sodium saccharin, cellulose, magnesium carbonate, and the like.

Topical formulations will generally take the form of suppositories or intranasal aerosols. For suppositories, traditional binders and excipients may include, for example, polyalkylene glycols or triglycerides; such suppositories may be formed from mixtures containing the active ingredient.

The amount of reagent administered will vary depending upon factors such as the nature of the reagent being used, the size and health of the patient, the nature of the condition being treated etc. in accordance with normal clinical practice. Typically, a dosage in the range of from 1 μg-50 mg/Kg for instance from 2-20 mg/Kg, such as from 5-15 mg/Kg would be expected to produce a suitable effect.

In a particular embodiment, when the agent is an IL-1 inhibitor, it may be for administration at a dose of 1-8 mg/kg body weight, preferably 1-4 mg/kg body weight, more preferably 1-2 mg/kg body weight.

The IL-1 inhibitor may be for administration at a dose of 75-600 mg/dose, preferably 75-300 mg/dose, more preferably 75-150 mg/dose.

The IL-1 inhibitor may be for administration at a dose of 100 mg/dose.

The dose may be adjusted if the patient is over- or underweight. Thus, an overweight patient may receive a dose higher than 100 mg, and an underweight person may receive a dose lower than 100 mg.

According to another embodiment, the IL-1 inhibitor is for administration at an interval of 24 hours to 6 months, preferably 48 hours to 2 months, more preferably, 72 hours to 1 month.

Importantly, the specific time interval between administration of the IL1-inhibitor is determined for each patient, depending on the specific condition, pain intensity and effect of the IL1-inhibitor.

The IL-1 inhibitor may be for administration once a day. If for administration once a day, the IL-1 inhibitor is preferably for administration at approximately the same time point each day. The, the IL-1 inhibitor may be for administration at an interval of 24 hours.

The, the IL-1 inhibitor may be for administration 1-2 times a week.

The, the IL-1 inhibitor may be for administration at an interval of 1-3 weeks.

The, the IL-1 inhibitor may be for administration at an interval of 1-6 months, such as 2-5 months or 3-4 months.

Further, according to another embodiment, the IL-1 inhibitor is for administration on-demand. Hence, the IL-1 inhibitor may be for administration when the patient is in need thereof. Some patients will need the IL-1 inhibitor to be more frequently and/or regularly administered while for other patients it will suffice to administer the IL-1 inhibitor on-demand when the pain cannot be managed otherwise.

Patients suffering from chronic inflammatory conditions and pain in the lower urinary tract have elevated levels of Substance P in urine, and thus this molecule acts as a diagnostic biomarker of pain. Hence, the invention further provides a method for diagnosing chronic inflammatory conditions in the lower urinary tract, said method comprising detecting elevated levels of Substance P in urine of a subject. Suitable detection methods are known in the art, and include ELISA. This method is particularly useful for diagnosing BPS.

In yet a further aspect, the invention provides a method for diagnosing susceptibility to chronic inflammatory conditions and pain in the lower urinary tract, said method comprising detecting Substance P in a urine sample obtained or obtainable from a subject, or a mutation in a gene encoding a protein selected from ASC or NLRP-3 which results in downregulation of said gene and/or in the expression of inactive protein, in a sample obtained or obtainable from a subject. Any appropriate sample may be used for identifying the genetic mutation, such as a blood, urine or saliva sample, or a buccal swab. As the applicants have previously demonstrated in WO2016/110818, absence of these proteins leads to increased susceptibility to IL-1β mediated conditions and chronic inflammatory conditions and pain in the lower urinary tract are herein identified as IL-1β mediated conditions.

Diagnosis may be carried out at the gene level, whereby the sequence of the Asc and/or Nlrp-3 is completely or partially determined and compared with a normal gene. For example, sites of common mutations that leads to inactivation or downregulation of the ASC or NLRP-3 proteins may be analyzed and the presence or absence of the selected mutation may be used to assess the likelihood that the patient is susceptible to cystitis.

Alternatively, diagnosis may be carried out at the protein level, where a suitable sample from a subject, such as a blood, serum, plasma or urine sample is analyzed for the presence of active Substance P or ASC or NLRP-3 protein. Suitable methods in this case may include immunochemical assays such as ELISAs which use antibodies specific for the target proteins.

Once diagnosed, administration to the subject of the proteins or functional equivalents thereof, would be expected to prevent or treat disease. Thus in yet a further aspect, the invention provides a method for preventing or treating chronic inflammatory conditions in the lower urinary tract in a patient susceptible thereto as a result of a mutation which impacts on the expression of functional ASC or NLRP-3, which method comprises administering to said patient a protein selected from ASC or NLRP-3 or a functional fragment or variant thereof or administering an effective amount of a reagent selected from the group consisting of interleukin-1 receptor antagonists and MMP inhibitors.

In a further aspect, the invention provides a protein selected from ASC or NLRP-3 or a functional fragment or variant thereof, for use in the treatment of patients suffering from or susceptible to chronic inflammatory conditions in the lower urinary tract as a result of a mutation which impacts on the expression of functional ASC or NLRP-3 respectively.

The inventors have also, surprisingly identified a further potential genetic basis for chronic pelvic pain syndrome, and in particular for chronic cystitis.

Accordingly, there is provided a method for diagnosing a chronic pelvic pain syndrome comprising identifying one of more variations in an IL-1 related gene in a sample obtained from a subject, when compared with the expected sequence, wherein the presence of the variation is indicative of the presence of or a predisposition to, especially an increased predisposition to a chronic pelvic pain syndrome.

The expected sequence means the gene sequence found in the majority of the population to which the subject belongs.

The method may comprise identifying more than one variation, such as 2, 3, 4, 5, 6, 7, 8, 9 or more variations.

The IL-1 related gene may be any gene that is involved in the IL-1 pathway, such as IL1A, IL1B, IL1RN, IL1R1, NLRP3, PYCARD, MMP7, TAC1 and TACR1.

In one embodiment, the IL-1 related gene is IL1A, in another embodiment the IL-1 related gene is IL1B, in another embodiment the IL-1 related gene is IL1RN, in another embodiment the IL-1 related gene is IL1R1, in another embodiment the IL-1 related gene is NLRP3, in another embodiment the IL-1 related gene is PYCARD, in another embodiment the IL-1 related gene is MMP7, in another embodiment the IL-1 related gene is TAC1, and in another embodiment the IL-1 related gene is TACR1.

Where the method comprises identifying more than one mutation, the second and/or further mutations may be present in any IL-1 related gene. In one embodiment, the IL-1 related gene is IL1A, in another embodiment the IL-1 related gene is IL1B, in another embodiment the IL-1 related gene is IL1RN, in another embodiment the IL-1 related gene is IL1R1, in another embodiment the IL-1 related gene is NLRP3, in another embodiment the IL-1 related gene is PYCARD, in another embodiment the IL-1 related gene is MMP7, in another embodiment the IL-1 related gene is TAC1, and in another embodiment the IL-1 related gene is TACR1.

In one embodiment, the method comprises identifying 2 or more, especially 3 or more variations in the IL1RN gene.

In a particular embodiment, the variation is a single nucleotide polymorphism, or SNP.

In one embodiment, the method comprises identifying a variation in at least one, at least two or at least three, at least four, at least five of rs113540343 (IL1A), rs4251972 (IL1RN) and rs10754558 (NLRP3), rs145268073 (NLRP3), and rs45507693 (IL1RN).

The sample may be any sample on which a genetic analysis may be carried out, such as saliva, blood or urine.

In the method of diagnosis, as in other aspects of the invention, the chronic pelvic pain syndrome may be chosen from a urological pain syndrome, a gynecological pain syndrome of the external genitalia, an internal pelvic pain syndrome and a gastrointestinal pelvic pain syndrome. Those syndromes may be further as defined in other aspects of the invention.

The method may also include the step of treating a subject identified by the steps of the method as having or being predisposed to chronic pelvic pain syndrome. The treatment may comprise administering an IL1 inhibitor, as previously defined. It may also, or alternatively, comprise administering a compound or composition that otherwise rectifies or modulates the effect of the variation.

In the methods of treatment or medical uses provided by the invention, the subject may also be a subject that has at least one variation in an IL-1 related gene, as previously defined.

As used herein, the expression 'fragment' and 'active fragment' refer to a peptide or protein which lacks one or more amino acids found in a full-length protein but which still has the function of the full-length protein.

As used herein, the expression 'variant' and 'active fragment' refer to a peptide sequence in which the amino acid sequence differs from the basic protein or peptide sequence in that one or more amino acids within the sequence are substituted for other amino acids. However, the variant produces a biological effect which is similar to that of the basic sequence.

Amino acid substitutions may be regarded as "conservative" where an amino acid is replaced with a different amino acid in the same class with broadly similar properties. Non-conservative substitutions are where amino acids are replaced with amino acids of a different type or class.

Amino acid classes are defined as follows:

| Class | Amino acid examples |
|---|---|
| Nonpolar: | A, V, L, I, P, M, F, W |
| Uncharged polar: | G, S, T, C, Y, N, Q |
| Acidic: | D, E |
| Basic: | K, R, H. |

As is well known to those skilled in the art, altering the primary structure of a peptide by a conservative substitution may not significantly alter the activity of that peptide because the side-chain of the amino acid which is inserted into the sequence may be able to form similar bonds and contacts as the side chain of the amino acid which has been substituted out. This is so even when the substitution is in a region which is critical in determining the peptide's conformation.

Non-conservative substitutions may also be possible provided that these do not interrupt the function of the protein or peptide.

Broadly speaking, fewer non-conservative substitutions will be possible without altering the biological activity of the polypeptides.

In general, variants will have amino acid sequences that will be at least 70%, for instance at least 71%, 75%, 79%, 81%, 84%, 87%, 90%, 93% or 96% identical to the basic sequence. Identity in this context may be determined using the BLASTP computer program with the basic native protein sequence as the base sequence. The BLAST software is publicly available at http://blast.ncbi.nlm.nih.gov/Blast.cgi (accessible on 12 Mar. 2009).

Variants may also include addition sequences such as tag sequences that may be used for instance in facilitating purification of the peptide or in detection of it. Thus for instance, the variant may further comprise an affinity tag such as chitin binding protein (CBP), maltose binding protein (MBP), glutathione-S-transferase (GST), FLAG, myc, biotin or a poly(His) tag as are known in the art. In another embodiment, the variant may comprise a fluorescent protein such as green fluorescent protein (GFP).

Other objectives, features and advantages of the present invention will appear from the following detailed disclosure, from the attached claims. It is noted that the invention relates to all possible combinations of features.

Generally, all terms used in the claims are to be interpreted according to their ordinary meaning in the technical field, unless explicitly defined otherwise herein. All references to "a/an/the [element, component, etc.]" are to be interpreted openly as referring to at least one instance of said element, component, etc., unless explicitly stated otherwise.

As used herein, the term "comprising" and variations of this term are not intended to exclude other components or integers.

FIGURE LEGENDS

The invention will now be described by way of example only with reference to the following figures, in which.

Figure 6:
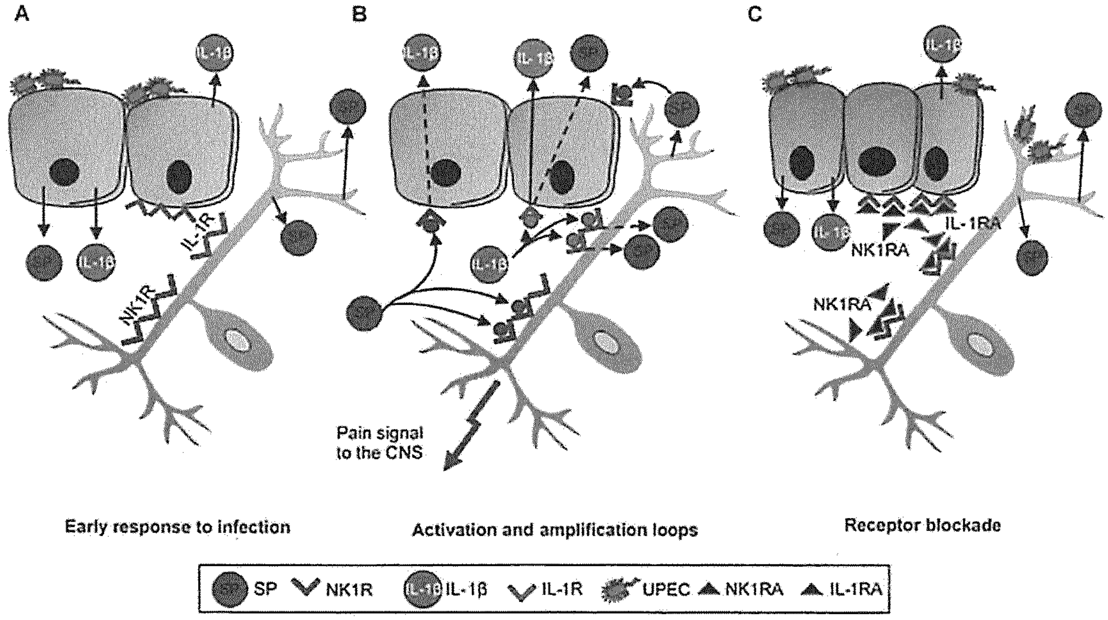

FIG. 6 is a schematic showing the IL-1β/Substance P loop as described in "Neuroepithelial control of mucosal inflammation in acute cystitis" by Butler, D. S. C. et al. (2018), Scientific Reports.

FIG. 7 shows a treatment outline for patients with chronic pelvic pain syndrome (FIG. 7*a*), patient descriptions (FIG. 7*b*), pain scores (FIG. 7*c*), frequency scores (FIG. 7*d*), quality of life scores (FIG. 7*e*) and urine SP concentrations (FIG. 7*f*).

FIG. 8. shows the summary of study protocol and results in example 3.

FIG. 9. Therapeutic effects of IL-1RA treatment in patients with bladder pain syndrome.

a) Ten patients with a long history of BPS were enrolled after informed consent and instructed to fill in a questionnaire detailing frequency of urination, pain, and quality of life. Laboratory samples were obtained at diagnosis, after the initiation of Anakinra treatment, during the "treatment break" and during long term follow up. b) Study outcome variables demonstrating an increased quality of life, due to reduced pain and frequency (Red=pretreatment samples. Blue=post treatment samples). Urine SP levels were markedly decreased. The data is shown for individual patients and lines indicate group medians. Wilcoxon signed rank test, P-values. c) Table showing treatment effects, side effects and long term treatment regimes in each patient.

Figure 10:
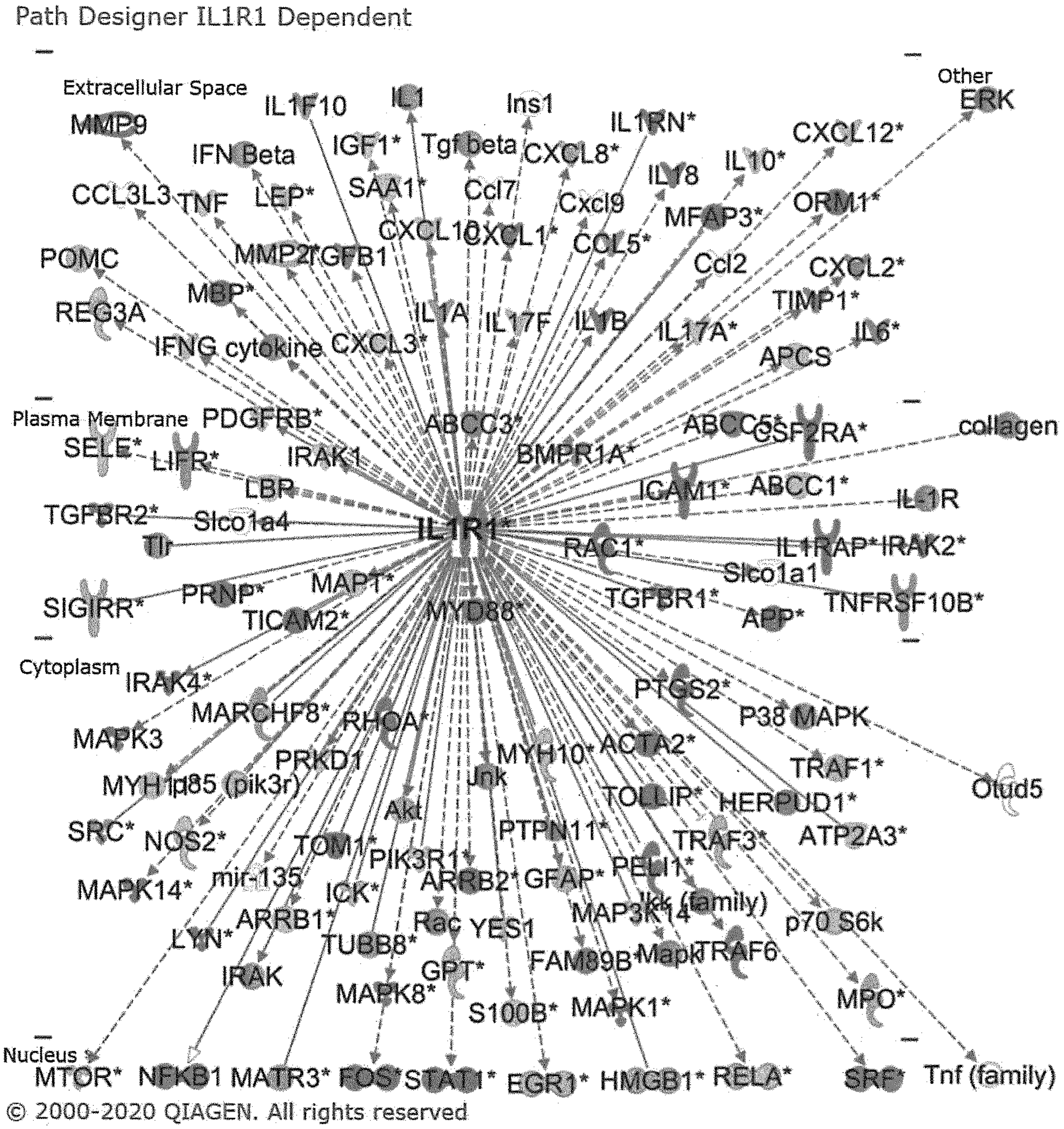

FIG. 10. IL-1RA treatment alters gene expression in patients with bladder pain syndrome.

a, Inhibition of gene expression, following Anakinra treatment. Heat map of significantly regulated pathways in individual patients. Orange=upregulated, Blue=downregulated (cut off FC 1.5, compared to individual pre-treatment samples). Inhibited pathways included neuroinflammation, IL-1- and inflammasome signalling, pattern recognition and adaptive immunity. b, IL-1R1 dependent gene expression network of PI showing significant inhibition of downstream genes (red=activated genes, blue=inhibited genes). c, Histograms of SNPs in rs113540343, rs4251972, rs10754558 and rs10199359 comparing frequencies of minor and major alleles between patients and the control NOMAD population. d, Table of the 10 most different SNPs between patients and the 1000 genomes control population.

Figure 11:
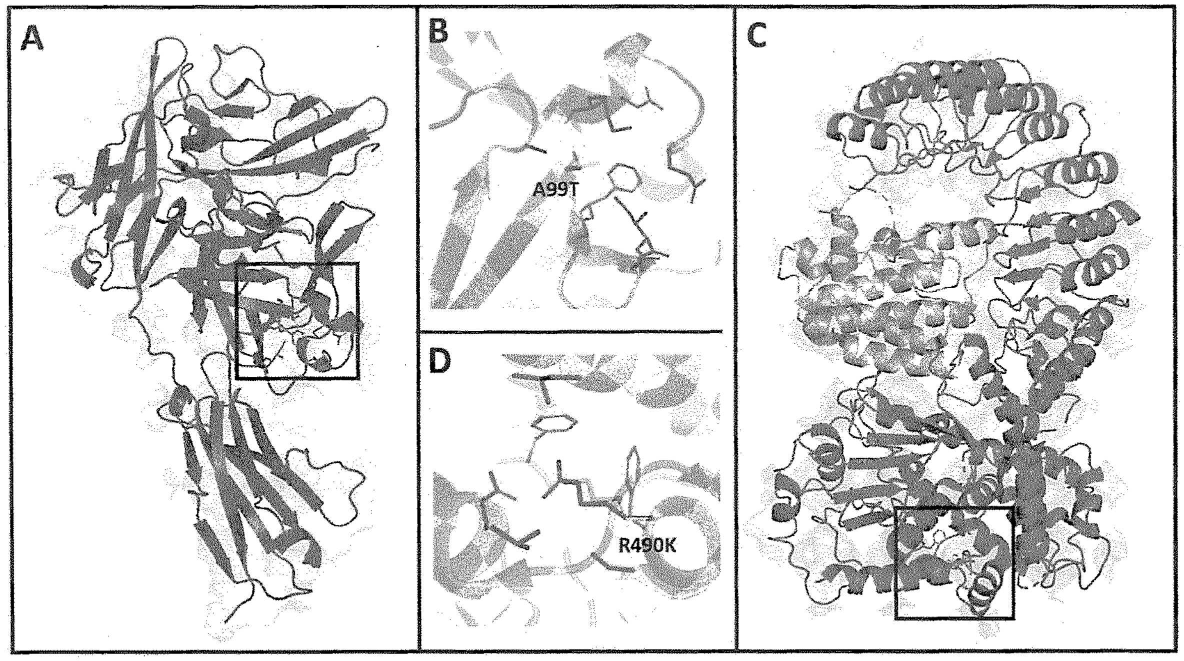

FIG. 11. Structural views of rs145268073 (NLRP3) and rs45507693 (IL1RN).

a) IL1RN (magenta) in complex with the ILR1 (cyan) (PDBID: 1IRA) is shown with the position of rs45507693 boxed. b) Local environment of rs45507693 with side chains reaching within 4 Å of the alanine 90 beta carbon (magenta) are shown. The mutation to threonine (yellow) will decrease the local hydrophobicity. c) NLRP3 shown in complex with the NEK7 kinase (salmon) (PDB ID: 6NPY) with the position of rs145268073 boxed. The mutation is positioned close to the ADP binding site and interface between the NB1-HD1 (red) and WHD-HD2-LRR (blue) modules. d) Local environment of rs145268073 illustrating its close proximity to the WHD-HD2-LRR (blue)/NB1-HD1 (red) interface that undergoes large structural changes upon inflammasome formation. Shown are also side chains reaching within 4 Å of the arginine 488 distal guanidinium group and the ADP molecule in the NB1-HD1 module.

DETAILED DESCRIPTION OF THE INVENTION

Example 1: IL1 Inhibitors for the Treatment of CPPS

The present teaching relates to the treatment of pain and pain related symptoms of chronic pelvic pain syndrome, wherein the method comprises administration of an IL1 inhibitor to a subject in need thereof.

The present teaching also relates to the alleviation of pain and pain related symptoms of chronic pelvic pain syndrome, wherein the method comprises administration of an IL1 inhibitor to a subject in need thereof.

The present teaching also relates to a method of reducing pain and pain related symptoms of chronic pelvic pain syndrome, wherein the method comprises administration of an IL1 inhibitor to a subject in need thereof.

According to one specific embodiment, an IL-1 inhibitor, such as an IL1-receptor antagonist, is used in a method of treating, alleviating or reducing pain and pain related symptoms of chronic pelvic pain syndrome. The chronic pelvic pain syndrome may be a urological pain syndrome, a gynecological pain syndrome of the external genitalia, an internal pelvic pain syndrome or a gastrointestinal pelvic pain syndrome. Specifically, the chronic pelvic pain syndrome may be prostate pain syndrome, bladder pain syndrome or urethral pain syndrome. The IL-1 receptor antagonist is preferably administered at a dose of 1-8 mg/kg body weight, preferably 1-4 mg/kg body weight, more preferably 1-2 mg/kg body weight. The IL-1 receptor antagonist is administered at an interval of 24 hours to 6 months, preferably 48 hours to 2 months, more preferably, 72 hours to 1 month. In certain cases, the IL-1 receptor antagonist is administered on-demand. The IL-1 receptor antagonist is administered by subcutaneous injection, intravenous injection, intramuscular injection, preferably as a subcutaneous injection. The IL-1 inhibitor may be chosen from anakinra, kanakinumab and diacerein.

According to another specific embodiment, the IL-1 inhibitor anakinra is used in a method of treating, alleviating or reducing pain and pain related symptoms of chronic pelvic pain syndrome. The chronic pelvic pain syndrome may be a urological pain syndrome, a gynecological pain syndrome of the external genitalia, an internal pelvic pain syndrome or a gastrointestinal pelvic pain syndrome. Specifically, the chronic pelvic pain syndrome may be prostate pain syndrome, bladder pain syndrome or urethral pain syndrome. Anakinra is administered at a dose of 1-8 mg/kg body weight, preferably 1-4 mg/kg body weight, more preferably 1-2 mg/kg body weight. Anakinra is administered at an interval of 24 hours to 6 months, preferably 48 hours to 2 months, more preferably, 72 hours to 1 month. In certain cases, anakinra is administered on-demand. Anakinra is administered by subcutaneous injection, intravenous injection, intramuscular injection, preferably as a subcutaneous injection. Generally, anakinra is administered as subcutaneous injection of 100 mg at an interval between 1 injection every two weeks to 2 injections per week. Preferably, the dose of anakinra is 100 mg, or less, as a subcutaneous injection, administered daily as a maximum, or intermittently, with shorter or longer intervals (days to months) according to the need of reducing symptoms and following the clinical response.

In other words, the IL-1 receptor inhibitor anakinra may be administered at a dose of 1-8 mg/kg body weight, preferably 1-4 mg/kg body weight, more preferably 1-2 mg/kg body weight. Thus, anakinra may be administered at a dose of 75-600 mg/dose, preferably 75-300 mg/dose, more preferably 75-150 mg/dose. Thus, anakinra may be administered at a dose of 100 mg/dose.

The dose of anakinra may be adjusted if the patient is over- or underweight. Thus, an overweight patient may receive a dose higher than 100 mg, and an underweight person may receive a dose lower than 100 mg.

Anakinra may be administered at an interval of 24 hours to 6 months, preferably 48 hours to 2 months, more preferably, 72 hours to 1 month. Importantly, the specific time interval between administration of anakinra is determined for each patient, depending on the specific condition, pain intensity and effect of anakinra. Thus, anakinra may be administered once a day. If administered once a day, anakinra is preferably administered at approximately the same time point each day. Thus, anakinra may be administered at an interval of 24 hours.

Anakinra may be administered 1-2 times a week or at an interval of 1-3 weeks or at an interval of 1-6 months, such as 2-5 months or 3-4 months.

Further, anakinra may be administered on-demand.

Anakinra may be administered by subcutaneous injection, intravenous injection, intramuscular injection. Preferably, anakinra is administered by subcutaneous injection.

Specifically, the present teaching discloses anakinra for use in a method of treating, alleviating or reducing pain and pain related symptoms associated with urological pain syndrome. The urological pain syndrome may prostate pain syndrome, bladder pain syndrome, scrotal pain syndrome, testicular pain syndrome, epididymal pain syndrome, penile pain syndrome, urethral pain syndrome or post-vasectomy scrotal pain syndrome, particularly prostate pain syndrome, bladder pain syndrome or urethral pain syndrome. Preferably, the dose of anakinra is 100 mg, or less, as a subcutaneous injection, administered daily as a maximum, or intermittently, with shorter or longer intervals (days to months) according to the need of reducing symptoms and following the clinical response.

Thus, the present teaching discloses anakinra for use in a method of treating, alleviating or reducing pain and pain related symptoms associated with bladder pain syndrome (BPS). The BPS may be bladder pain syndrome type 3c. Preferably, the dose of anakinra is 100 mg, or less, as a subcutaneous injection, administered daily as a maximum, or intermittently, with shorter or longer intervals (days to months) according to the need of reducing symptoms and following the clinical response.

The present teaching also discloses anakinra for use in a method of treating, alleviating or reducing pain and pain related symptoms associated with prostate pain syndrome (PPS). Preferably, the dose of anakinra is 100 mg, or less, as a subcutaneous injection, administered daily as a maximum, or intermittently, with shorter or longer intervals (days to months) according to the need of reducing symptoms and following the clinical response.

Furthermore, the present teaching discloses anakinra for use in a method of treating, alleviating or reducing pain and pain related symptoms associated with urethral pain syndrome (UPS). Preferably, the dose of anakinra is 100 mg, or less, as a subcutaneous injection, administered daily as a maximum, or intermittently, with shorter or longer intervals (days to months) according to the need of reducing symptoms and following the clinical response.

Example 2: Anakinra for Use in Chronic Inflammatory Conditions

Here we identify that IL-1RA treatment may be useful to alleviate bladder pain. The hypothesis was evaluated by enrolling ten patients with chronic pelvic pain syndrome, (CPPS) in an investigator driven open trial (see below and FIG. 7). The patients received daily anakinra treatment (100 mg) until a stable response was observed. Treatment was then transiently interrupted and when the symptoms returned, treatment was resumed. Patient 10 remained asymptomatic.

Dramatic clinical effects were observed in 9/10 patients, who experienced a reduction in symptom score (pain and frequency, $P<0.01$) and increase in quality of life ($P<0.02$). Urine neuropeptide levels were markedly reduced ($P<0.001$) and at the RNA level, anakinra treatment inhibited neuroinflammation and IL-1-dependent gene expression. One patient did not respond.

Current therapeutic options in CPPS patients include antibiotics, non-steroidal anti-inflammatory drugs, opioids such as morphine and antidepressants. Bladder ulcers may be surgically removed, but in most cases, surgery has no lasting effect. This study suggests that IL-1R inhibition may offer a new molecular approach to treating cystitis and bladder pain, with the potential to improve the quality of life in patients, who so far has been offered little to alleviate their suffering.

The applicants have performed an open Anakinra trial in patients with chronic inflammatory conditions in the lower urinary tract, specifically chronic cystitis and CPPS. This structured observational study to investigate the effect of treatment with Anakinra in patients suffering from chronic cystitis and CPPS.

Overview of Patient Visits

Inclusion visit: Patient is informed about the study and is included after signed informed consent is obtained. A structured interview and clinical investigation is performed. The disease severity is evaluated using a symptom score. Follow-up visits are booked.

Samples: Blood and urine samples for investigation of inflammatory processes as well as genetic and proteomic analyses.

Visit 1:

A structured interview and clinical investigation is performed. Symptom severity is recorded.

Treatment with Anakinra is started and continued for seven days (until next visit).

Samples: Blood and urine samples for investigation of inflammatory processes as well as genetic and proteomic analyses.

Visit 2:

Evaluation of effect after one week of treatment with Anakinra. A structured interview and clinical investigation are performed. Symptom severity is evaluated. Patients with no treatment effect are excluded from further treatment.

Patients exhibiting a positive effect of the treatment make a pause in the treatment for two weeks (or at least long enough for the clinical effect of the treatment to wane).

Samples: Blood and urine samples for investigation of inflammatory processes as well as genetic and proteomic analyses.

Visit 3:

Follow-up after treatment pause. A structured interview and clinical investigation is performed. Symptom severity is evaluated. If the patient has relapse, Anakinra treatment is resumed.

Samples: Blood and urine samples for investigation of inflammatory processes as well as genetic and proteomic analyses.

Visit 4:

Follow-up with evaluation of effect after three weeks of treatment with Anakinra. A structured interview and clinical investigation is performed. Symptom severity is evaluated.

Patients pause the treatment for two weeks (or at least long enough for the clinical effect of the treatment to wane).

Samples: Blood and urine samples for investigation of inflammatory processes as well as genetic and proteomic analyses.

Visit 5:

Final visit after pause of treatment with Anakinra. A structured interview and clinical investigation is performed. Symptom severity is evaluated.

Samples: Blood and urine samples for investigation of inflammatory processes as well as genetic and proteomic analyses.

Figure 1:
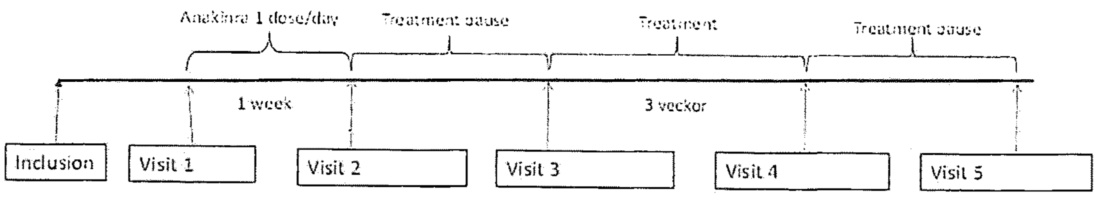
FIG. 1 shows a treatment outline for patients with chronic pelvic pain.

The visit programme is set out diagramatically in FIG. 1.

Methods

Clinical Investigation of Symptom Severity:

During patient visits, structured interviews evaluating symptoms (including consumption of medications) and clinical investigations are performed. Throughout the study period, the patients make daily symptom scores regarding pain, urination, sense of urgency and quality of life following a structured formula.

Inflammatory Parameters:

For evaluation of the levels of systemic and local inflammatory processes, analyses of CRP, neutrophil count and Interleukins are performed in serum and urine.

Genomics and Proteomics

Blood samples for DNA- and RNA-analyses as well as urine samples for proteomics are obtained throughout the study.

Monitoring:

Results are registered continuously within the clinical chart of each patient. Patient visits in the study are, to a large extent, part of regular patient management visits.

Results

Clinical Investigation of Symptom Severity

The treatment was proven effective in 60% of the patients as determined by a decrease in symptom scoring. Interestingly, all nine responding patients had Hunner's lesions, indicating that treatment might be more effective in this patient group. The patients were subsequently taken off treatment to investigate if the treatment was curative or whether symptoms would reappear. The symptoms ultimately came back, and the patients were again put back on anakinra treatment.

TABLE 1

| Trial Results | | |
|---|---|---|
| Patients Recruited | Symptom Score Decrease at 1 week of treatment | Symptom Score No Decrease at 1 week of treatment |
| 15 | 9 | 6 |

Figure 2:
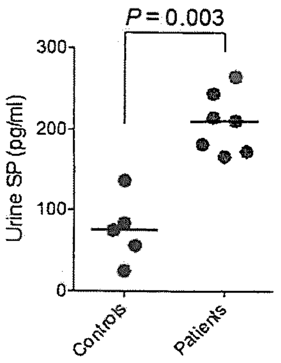
FIG. 2 is a chart showing elevated urine Substance P (SP) levels in patients with chronic cystitis before treatment.
Figure 3:
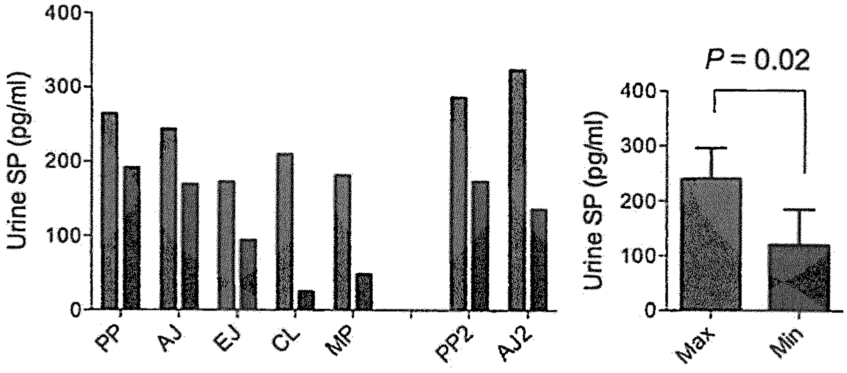
FIG. 3 is a series of charts showing urine SP levels is reduced in after Anakinra treatment in patients with chronic cystitis.
Figure 4:
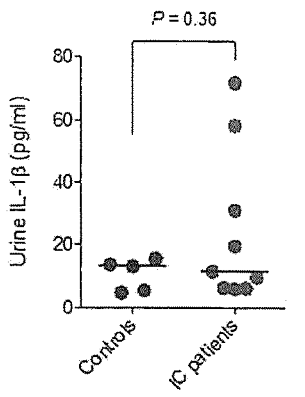
FIG. 4 is a chart showing no change in urine IL-1β in patients with chronic cystitis before Anakinra treatment
Figure 5:
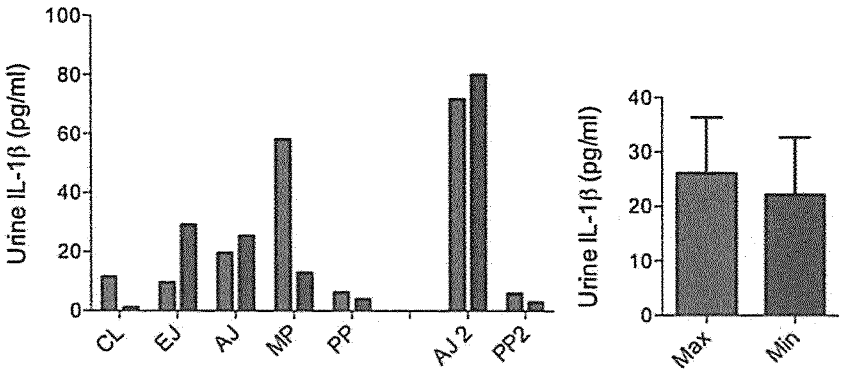
FIG. 5 is a series of charts showing urine IL-1β levels do not change after Anakinra treatment in patients with chronic cystitis.

Inflammatory Parameters:

To be able to define a treatment group where anakinra might serve as an effective therapeutic option, we searched for urine biomarkers. In addition to patient urine samples, samples were collected from healthy controls to compare urine concentrations of IL-1β and Substance P (SP). Surprisingly there was no IL-1β present in the urine of patients during maximum symptoms, nor in the control urine (13.2 vs 11.6 pg/ml) (FIG. 4) and urine IL-1β levels do not change after Anakinra treatment in patients (FIG. 5). In contrast, SP concentrations was increased in patients during maximum symptoms (209 vs 75 pg/ml, P=0.003), indicating a biomarker for bladder inflammation (FIG. 2). SP concentrations was subsequently analysed during the time of maximum symptom with paired samples from the time of minimum symptom showing a marked decrease after treatment (243 vs 136 pg/ml, P=0.02) (FIG. 3).

Study Protocol and Results

Ten patients with a long history of CPPS were enrolled after informed consent (age, gender, disease profile) and instructed to fill in a questionnaire detailing frequency of urination, pain, frequency of pain medication and quality of life.

The time to symptom relief after the first dose varied (1-6 hours) as did the duration (0.5-8 days), resulting in individualised treatment regimens (FIG. 7*a*). Two patients reported local irritation at the injection site and one patient developed neutropenia (FIG. 7*b*). A shared effect pattern included an initial response, resurgence of pain when treatment was interrupted and a return of pain relief and ease of urination when therapy was resumed.

A significant reduction in pain, urgency and frequency of urination was recorded in 9/10 patients (FIGS. 7*c*, 7*d* and 7*e*). Laboratory samples were obtained at diagnosis, after the initiation of anakinra treatment (n=10), during the "treatment break" and after continuation of anakinra treatment (n=9). Urine neuropeptides involved in the pain response (Substance P) were inhibited, with a biphasic response following the symptom score (FIG. 7*f*).

Gene expression analysis of peripheral blood RNA revealed a reduction in neuro-inflammation, following anakinra treatment.

Clinical Results

The effect of anakinra in the treatment of CPPS was studied in a clinical study. Inclusion criteria were CPPS mainly with the Bladder Pain phenotype, but also the with the Urethral and Prostate Pain phenotype. Exclusion criteria were uncontrolled diabetes mellitus, treatment for malignant disease within the preceding 10 years, pregnancy and age<18 years and ongoing infectious diseases, including urinary tract infections, and neutropenia (<$1.5\times10^9$/L). Patients gave informed consent for the use of unidentified personal clinical data for research purposes. Included patients were examined using clinical standard methods to rule out any ongoing disease. Blood and serum for hemoglobulin, liver and kidney function tests and White Blood Cell (WBC) counts were analysed. Urine was obtained for dip stick test (leukocytesteras for WBC estimation, the nitur test for ruling out bacteriuria), standard urinary Interleukins (IL6, IL8 and IL1b) and for urine culture. Cystoscopy and CT urography were performed in all patients. Blood and serum analysis and cystoscopy were repeated approximately two weeks after the start of treatment, and after approximately three months. Nine patients were recruited (Table 2).

After inclusion, patients were treated with anakinra 100 mg by self-administrated subcutaneous injection, repeated once daily as a maximum, or (if relief of symptoms and pain) on demand when symptoms or pain recurred. Regularly symptom scoring on frequency, supra-pubic/bladder pain/prostate/urethral pain and Quality of Life was performed to evaluate treatment effect.

TABLE 2

| Patient characteristics and diagnosis | | | | | | | |
|---|---|---|---|---|---|---|---|
| No | Age (years) Gender (M/F) | CIC/ Cath | CPPS/ main subtype | Symptom duration (year/s) | Cystoscopy finding Type 3c yes/no | Histology | Concomitant diseases, comment |
| 1 | 61 M | CIC | BPS Type 3c | 2 | yes | inflamm. | partial tetraparesis, neurogenic bladder, kidney stone |

TABLE 2-continued

Patient characteristics and diagnosis

| No | Age (years) Gender (M/F) | CIC/ Cath | CPPS/ main subtype | Symptom duration (year/s) | Cystoscopy finding Type 3c yes/no | Histology | Concomitant diseases, comment |
|---|---|---|---|---|---|---|---|
| 2 | 67 M | — | BPS Type 3c | >10 | yes | inflamm. | benign prostate hyperplasia |
| 3 | 77 F | Cath | BPS Type 3c | 2 | yes | inflamm. | small contracted bladder, previous irradiation due to gynecological cancer, COPD |
| 4 | 67 F | — | BPS Type 3c | >10 | yes | nd | healthy otherwise |
| 5 | 39 F | — | BPS | 1 | no | nd | healthy otherwise |
| 6 | 70 F | — | BPS | >10 | no | nd | Mb Dercum |
| 7 | 20 F | — | UPS | <1 | no | nd | healthy otherwise |
| 8 | 70 M | — | PPS | <1 | no | nd | healthy otherwise |
| 9 | 65 M | — | BPS | >10 | yes | cystitis cystica | unspecified intermittent fever, arthralgia |

Notes to Table 2

M = Male, F = Female; CIC = Clean Intermittent Catheterization; Cath = Indwelling catheter, CPPS = Chronic Pelvic Pain Syndrome; BPS Type 3c = Bladder Pain syndrome Type 3c; BPS = Bladder pain Syndrome; UPS = Urethral Pain Syndrome; PPS = Prostate Pain syndrome; Cystoscopy finding Type 3c = finding of Hunner's ulcera; inflamm. = inflammation corresponding with Hunner's ulcera. In patient 5 a non-specific scattering of red lesions was found at cystoscopy. Histological specimen was not taken. Repeat cystoscopy after 2 weeks of treatment revealed a normal bladder mucosa. In patient 9 cystoscopy revealed a "cystitis cystica", or cystitis cystica glandularis, a specific benign inflammation due to chronic irritation or by unknown causes. In all other patients cystoscopy was normal. All cystoscopy findings refer to findings at inclusion in the study, except Patient 3 who was diagnosed with Hunner's ulcera one year prior to inclusion in the study (se detailed patient description below), nd = not determined; COPD = chronic obstructive pulmonary disease Notably, all patients responded with dramatically reduced symptoms as measured by symptom scoring (Table 2). The maximum effect on symptoms after one s.c. inj. of 100 mg anakinra was seen within 1 to 24 hours and the maximum effect generally lasted 2-3 days. One patient (No 5) experienced the maximum effect for 8 days. In one patent (No 3), the maximum effect lasted only up to 13 hours, but generally, the maximum effect remained for several days. Thus, for the majority of patients, anakinra is administered one to two times a week at a dose of 100 mg s.c.

Notably, the number of micturitions during daytime was reduced in all patients and also number of micturitions at night-time was generally reduced.

The pain experienced by the patients was decreased dramatically and five out of the nine patients were even completely free from pain.

In addition, the experience quality of life (QoL) increased in all patients.

TABLE 3

Effect and duration of anakinra treatment in patients with Chronic Pelvic Pain/Bladder//Urethral/Prostate Pain Syndrome

| | Evaluation of anakinra treatment effect | | | | | | | | |
|---|---|---|---|---|---|---|---|---|---|
| | Onset | Duration | Frequency (nycturia) | | Pain | | QoL reduction | | Side |
| No | (hours) | (d/h) | pre | post | pre | post | pre | post | effect |
| 1 | 2 | 2-3 d | 8 (1-2) | 5 (0) | 5 | 0 | 5 | 0 | not reported |
| 2 | 4-6 | 1-2 d | 12 (5) | 5 (1) | 5 | 2 | 5 | 2 | local s.c. irritation |
| 3 | 1-2 | 7-13 h | — | — | 5-6 | 1 | 5-6 | 1 | not reported |
| 4 | 1-2 (12) | 1-3 d | 11 (3) | 4 (1) | 6 | 0 | 6 | 0 | not reported |
| 5 | 1 | 8 d | 12 (3) | 6 (1) | 4 | 0 | 4 | 0 | headache post inj. |
| 6 | 2 | 3 d | 12 (5) | 6 (1) | 4 | 0 | 4 | 0 | local s.c. irritation |

TABLE 3-continued

Effect and duration of anakinra treatment in patients with Chronic Pelvic Pain/Bladder//Urethral/Prostate Pain Syndrome Evaluation of anakinra treatment effect

| No | Onset (hours) | Duration (d/h) | Frequency (nycturia) pre | Frequency (nycturia) post | Pain pre | Pain post | QoL reduction pre | QoL reduction post | Side effect |
|---|---|---|---|---|---|---|---|---|---|
| 7 | 24 | 3 d | 12 (4) | 6 (1) | 4 | 1 | 4 | 1 | not reported |
| 8 | 2 | 2 d | 8 (5) | 8 (2) | 4 | 2 | 6 | 2 | not reported |
| 9 | 3 | 3 d | 7 (1) | 4 (1) | 5 | 0 | 5 | 0 | not reported |

Notes to Table 3

Treatment was given all patients with anakinra 100 mg as a subcutaneos (s.c.) injection (inj.) with a maximum frequency of once daily, or after recurrence of Symptoms Obs./Treatm. = Observation/Treatment; Onset = time for maximum effect on symptoms after one s.c. inj. of 100 mg anakinra; Duration = time of lasting maximum effect after one s.c. inj. of 100 mg anakinra; d/h = days/hours; Frequency (nycturia) = Number of micturations during daytime and nighttime (the latter number within paranthesis); QoL = Quality of Life; Pain and QoL reduction estimated by interview and scored by 0-6 with 0 meaning symptom-free/not reduced QoL and 6 being severe pain and severely reduced QoL Side effect = reported side effects were mild. Local s.c. irritation = approx. 4 cm big red and edematous skin reaction at the place of injection, symptomatically; treated with hydrocortison application. Headache post inj. = moderate headache treated with analgetics such as paracetamol.

Long-term follow-up (Table 3) revealed that all nine patients experienced a highly increased, or increased, quality of life. The treatment effect in all patients was consistent during long-term follow-up.

Estimated WBC and Interleukins in urine were not significantly increased prior, during or after treatment.

If cystoscopy revealed Hunner's ulcera prior to treatment, this finding was unchanged at follow up cystoscopy. In one patient (patient 5), a non-specific scattering of small red lesions disappeared after treatment.

Side effects were sparse and mild; two cases of skin reaction at the place of injection, treated by hydrocortisone application, and one case of headache post injection (patient 5), treated occasionally with paracetamol and NSAID.

TABLE 4

Long-term follow-up of patients

| No | Obs time (days) | Anakinra (s.c. 100 mg) long-term treatment regimen | Comment |
|---|---|---|---|
| 1 | 397 | 1 per week | highly increased QoL; after 6 months: treatment paus (ureteric stone) |
| 2 | 274 | 1 per 2-4 weeks | increased QoL, after 3 months long lasting symptom free |
| 3 | 203 | 1 per day | highly increased QoL, planned cystectomy postponed |
| 4 | 173 | 1 per week | highly increased QoL |
| 5 | 121 | 1 per 2-3 days | highly increased QoL |
| 6 | 111 | 1 per 2-3 days | highly increased QoL |
| 7 | 38 | 1 per week | increased QoL |
| 8 | 33 | 1 per 2-3 days | increased QoL |
| 9 | 24 | 1 per week | highly increased QoL, |

Below is a detailed description of each patient.

Patient 1: 61 year old male with a previous history of traumatic spinal cord injury resulting in a neurogenic bladder disorder (hyperreflexia in combination with low detrusor function) treated with clean intermittent catherization. Two years prior to inclusion the patient had onset of dysuria, urge and pain from the bladder, with urine cultures only intermittently showing uropathogenic growth. Antibiotic treatment did not relieve the symptoms. Cystoscopy demonstrated a Hunner's ulcera. Treatment with transurethral resection and coagulation of the lesion as well as intravesical therapy with intravesical glycosaminoglycan (GAG) layer replenishment therapy did not result in subjective improvement. The patient was treated with little benefit with maximum dosages of peroral drugs against urgency (Mirabegron and anticholinergics) and with non-morphine analgesics. After administration of anakinra 100 mg s.c. (subcutaneous) with a dosage of approximately one injection per week, the patient was subjectively significantly improved with a clear reduction in frequency and local pain from the bladder. He is at the present under intermittent on-demand self-treatment with anakinra since more than one year with a stable treatment effect and without side effects.

Patient 2: Male 67 years old. History of more than 20 years of Bladder Pain Syndrome and benign prostate hyperplasia with outflow obstruction. Five years prior to inclusion a transurethral resection of the prostate including a coagulation/resection of a Hunner's ulcera in the bladder gave long-term symptom relief. Since one year recurring of symptoms with bladder pain, urge, and frequent nycturia, which the patient managed with the use of non-morphine analgesics and non-steroid anti-inflammatory drugs (NSAID). Cystoscopy revealed an incipient Hunner's ulcera. Anakinra treatment was initiated, which was followed by significant symptom and pain relief. The patient is at the present under on demand self-treatment, with approximately 1 injection of 100 mg anakinra (100 mg) per 2-3 weeks.

Patient 3: Female 77 years old. More than 20 years prior to inclusion successfully treated for gynecological cancer with irradiation and hysterosalpingo-oophorectomy. Chronic obstructive pulmonary disease. One year prior to inclusion start of urge and frequency, including local pain. Cystoscopy revealed a Hunner's ulcera in the bladder. Treatment with transurethral resection and coagulation of the lesion as well as intravesical therapy with intravesical glycosaminoglycan (GAG) layer replenishment therapy did not result in subjective improvement. After a few months, the bladder contracted and the patient was forced to be treated by indwelling catheter. The bladder pain was worsened and treated with morphine and corticosteroids. At inclusion the patient was on a waiting list for cystectomy. Cystoscopy prior to treatment did not reveal any bladder inflammation, other than normally found when indwelling catheter is used. After start of anakinra treatment pain relief followed immediately, and morphine and corticosteroid, treatment was ceased. At present the patient is on regular once daily anakinra self-administrated treatment, and the cystectomy is postponed.

Patient 4: Female 67 years old. Otherwise healthy female with a history of Bladder Pain Syndrome since more than 10 years. After an initial resection and coagulation, the patient has been symptom free. One year prior to inclusion the symptoms with urge and local pain recurred but treatment with non-morphine analgesics and NSAID gave little effect. Cystoscopy revealed an incipient Hunner's ulcera and treatment with anakinra was started which resulted in a constant relief of symptoms. The patient is at the present on one weekly injection of anakinra 100 mg s.c., which gives complete symptom relief.

Patient 5: Female 39 years old. Otherwise healthy, but with occasionally migraine attacks. Six months prior to inclusion slowly worsening urge and frequency, including local pain from the bladder. Cystoscopy revealed small red lesions in the bladder but without inflammation. The patient was treated with little benefit with maximum dosages of per oral drugs against urgency (Mirabegron and anticholinergics) and with non-morphine analgesics. Anakinra treatment resulted in constant relief of symptoms. The patient is at present under self-administrated treatment with anakinra 100 mg s.c. once per 1-2 weeks. After each injection, the patient gets minor headache, treated with NSAID and paracetamol. Repeated cystoscopy has demonstrated a normal bladder mucosa.

Patient 6: Female 70 years old. More than 20 years prior to inclusion diagnosed with Mb Dercum (adiposa dolorosa) and during the same period bladder pain including urge and frequency resulting in micturition once per hour, also during night-time. On cystoscopy, a normal bladder mucosa was found. Treatment with non-morphine analgesics, corticosteroids, anticholinergic drugs and mirabegron was not effective. After anakinra treatment started the patient did not have symptoms, or nearly no symptoms, from her adiposa dolorosa, and the urge, frequency and bladder pain dramatically decreased. She is at present on anakinra treatment 100 mg s.c with two injections per week.

Patient 7: Female 20 years old. Otherwise healthy. Six months prior to inclusion she had urethral pain and increased urgency, resulting in micturition once per 2 hours day and night. Treatment with local corticosteroid instillation in the urethra, non-morphine analgesics, corticosteroids, anticholinergic drugs and mirabegron was not effective. Cystoscopy was normal. After anakinra treatment, her symptoms urgency was dramatically reduced. The urethral pain was significantly reduced but recurred transiently. She is at present on anakinra treatment 100 mg s.c one injection per week.

Patient 8: Male 70 years old. Under treatment for hypertonia and atrial fibrillation. Six months prior to inclusion significant symptoms with severe urge and frequency in combination with prostate pain. The patient was forced to micturition every hour day and night. Examinations revealed a normal but tender benign prostate, cystoscopy and MR of the small pelvis and the prostate were all normal. Treatment with antibiotics (ex juvantibus), anticholinergic drugs and mirabegron was not effective. After starting anakinra treatment 100 mg s.c. injection the urgency and frequency was dramatically reduced. The prostate pain was reduced significantly, but recurred transiently. At present, the patient is under on-demand treatment with anakinra 100 mg s.c. injection.

Patient 9: Male 65 years old. Since more than 10 years with intermittent fever and arthralgia, without known cause in spite of extensive investigations by the rheumatoid department. Ten years prior to inclusion diagnosis of cystitis cystica (benign granulomatous inflammation) in the bladder. Increased urgency and frequency, but without the need for treatment. After anakinra treatment with 100 mg s.c. injection, the patient reported relief of fever attacks and arthralgia, as well as reduced urgency and frequency. At present the patient is under anakinra treatment 100 mg. s.c. injection twice per week.

Example 3: Treatment of BPS

The bladder pain syndrome (BPS) destroys careers, social life and sexual health, as patients experience debilitating pain, extreme frequency and urgency of urination. Numerous therapeutic approaches have been tested but except for the use of antibiotics to treat super-infections or pain medications, therapeutic success has been limited and patients are often severely handicapped. The molecular basis of BPS has also remained an enigma, precluding the development of more specific therapeutic alternatives.

By analysing the inflammatory phenotype in acute cystitis, the recently identified IL-1 as a cause of acute bladder pathology, aggravated by a genetic predisposition affecting the inflammasome constituents Asc and Nlrp3. The IL-1 receptor antagonist, Kineret (anakinra), dramatically reduced bladder inflammation and increased bacterial clearance in a murine cystitis model (ref). IL-1R blockade also affected the pain receptor NK1R in the bladder mucosa, linking IL-1 dependent inflammation to the pain response.

The inventors have tested the hypothesis that IL-1RA treatment may be useful to alleviate bladder pain. Ten patients with BPS were enrolled in an investigator-driven open trial. The patients received daily Kineret treatment (100 mg) for seven days. Treatment was then transiently interrupted and if the symptoms returned, treatment was resumed.

Dramatic clinical improvement was observed in 9/10 patients. A shared effect pattern included an initial response, resurgence of pain when treatment was interrupted and a return of pain relief and ease of micturition when therapy was resumed. One patient responded only transiently.

The patients experienced a reduction in symptom score (pain and frequency, $P<0.01$) and a marked increase in quality of life ($P<0.02$). At enrolment, elevated levels of neuropeptides controlling the pain response were detected in urine. A rapid reduction occurred after the initial Kineret treatment period and again when treatment was resumed after the treatment break ($P<0.001$). Gene expression was also inhibited, affecting neuroinflammation, Toll-like receptor dependent pattern recognition and IL-1-signalling.

Current therapeutic options in BPS patients include non-steroidal anti-inflammatory drugs, opioids such as morphine and experimental intravesical treatments. Bladder ulcers may be surgically removed, but in most cases, surgery has no lasting effect. This study suggests that IL-1R inhibition may offer a new molecular approach to treating cystitis and bladder pain, with the potential to improve the quality of life in patients, who so far has been offered little to alleviate their suffering.

a) Schematic of the study protocol. Ten patients with a long history of BPS (ref EAU guidelines) were enrolled after informed consent and instructed to fill in a questionnaire detailing frequency of urination, pain, frequency of pain medication and quality of life. Laboratory samples were obtained at diagnosis, after the initiation of Kineret treatment (n=10), during the "treatment break" and after continuation of Kineret treatment (n=9). Neuropeptides involved in the pain response (Substance P) were quantified in urine. Peripheral blood RNA was subjected to genome wide transcriptomic analysis to define molecular effects of Kineret treatment.

b) Study outcome variables demonstrating an increased quality of life and a reduction in frequency, pain and urine SP levels (Red=pretreatment samples. Blue=post treatment samples). The time to symptom relief after the first dose varied (1-6 hours) as did the duration (0.5-8 days), resulting in individualised treatment regimens. Two patients reported local irritation at the injection site, which was treated with local steroids. The data is represented as individual patients and the median. The data was analysed using Wilcoxon signed rank test, P-values less than 0.05 was considered significant.

c) Patient characteristics, underlying disease and outcome. Inflammation of the bladder in six patients was defined by cystoscopy and confirmed by histology. The mucosal cell infiltrate included mast cells and lymphocytes ref).

d) Inhibition of gene expression, following Kineret treatment. Heat map of significantly regulated pathways in individual patients Orange=upregulated, Blue= downregulated (cut off FC 1.5, compared to each individual pretreatment sample). Inhibited pathways included neuro-inflammation, IL-1- and inflammasome signalling, pattern recognition and adaptive immunity. Fold change of significantly regulated genes are shown in Table 2 (means of nine patients).

Example 4

The immune response to infection must be exquisitely controlled and balanced. Deficiencies affecting cellular immune functions create an inadequate defense and increase the susceptibility to infection. Conversely, over-active immune responses are classically associated with diseases like asthma, rheumatoid arthritis and diabetes and treatments aim to return the immune balance and hinder disease progression.

Innate immunity controls the immediate response to infection, especially at mucosal surfaces where the initial contact between microbes and their host usually takes place. Detailed genetic studies have clearly shown that single gene defects control both the susceptibility to acute infection and the risk for chronicity and tissue damage. Specific immune activation pathways and immune effector functions have been identified and include Toll-like receptors, transcription factors, inflammasome, inflammatory cells.

The damaging potential of innate immune hyper-activation is highly relevant for the urinary tract, which is exposed to bacteria in everyone but leads to disease only in some. UTIs are extremely common, as about 50% of all women experience at least one episode during their lifetime. Many develop socially debilitating recurrent infections and therapeutic options are becoming extremely limited, due to the increase in antibiotic resistance.

The molecular basis of acute cystitis has been unresolved until recently, when Interleukin 1 (IL-1) hyper-activation was shown to drive acute disease severity and tissue damage. Paradoxically, disruption of the NACHT, LRR, PYD domains-containing protein 3 (Nlrp3) inflammasome created severe acute cystitis in infected mice, accompanied by IL-1 hyper-activation and a pain-sensing loop involving neurokinin 1 receptor (NK1R) and substance P (SP). $Asc^{-/-}$ and $Nlrp3^{-/-}$ mice developed rapid, fulminant bladder inflammation and tissue damage, accompanied by massive neutrophil infiltration, hyper-activation of IL-1 beta and IL-1 beta-dependent gene networks. The severe disease phenotype was explained by a non-canonical processing mechanism in the Nlrp3 inflammasome-deficient mice, where overexpression of Matrix Metallopeptidase 7 (MMP7), resulted in highly efficient pro-IL-1beta processing. Finally, Asc and Nlrp3 were identified as transcriptional mmp7 repressors explaining why MMP7 is overexpressed in $Asc^{-/-}$ and $Nlrp3^{-/-}$ mice. In stark contrast, $Il1^{-/-}$ mice were protected from infection, and did not show any signs of bladder inflammation, further emphasizing the importance of IL-1 as a driver of symptoms and pathology.

The IL-1 receptor antagonist (IL1-RA) Anakinra (brand name Kineret) is a biological immunomodulant, with an excellent safety record when used for indications such as rheumatoid arthritis. The therapeutic potential of IL-1 inhibition was examined in inflammasome-deficient mice developing severe cystitis. Anakinra was shown to dramatically reduce bladder inflammation and accelerate bacterial clearance. IL-1R blockade also reduced the expression of the pain receptor NK1R and its ligand SP in the bladder mucosa, linking IL-1 dependent inflammation to the pain response in the bladder mucosa[3]. The dramatic disease phenotype in NLRP3 inflammasome deficient mice and the therapeutic effect of Anakinra suggested that these mechanisms might be relevant in patients with chronic pelvic pain, which is often attributed to recurrent episodes of cystitis.

In this study, we addressed if IL-1RA treatment might be efficient in patients with chronic bladder pain. We conducted an explorative, open label trial in patients with BPS (Table 5). Patients received daily subcutaneous injections of Anakinra (100 mg) for seven days and the therapeutic effects were recorded. To address potential placebo effects, treatment was transiently interrupted for a maximum of 14 days and when the symptoms returned, treatment was resumed and continued with individual treatment regimes. At enrolment, cystoscopy revealed signs of Hunner's lesions in six of the patients, confirmed by histopathology. In the remaining patients, bladder pathology was not detected. During the study, patients were instructed to keep a symptom journal recording the sensation of pain and the frequency of micturition.

The immediate subjective response of the patients was remarkable. Dramatic clinical improvement was observed in 9/10 patients. A shared initial effect pattern included rapid symptom relief at the onset of treatment (median=2 hours) with lasting therapeutic effects (3 days). Dramatic clinical improvement was observed in all patients after the first 7 days, who experienced a reduction in symptom score (pain and frequency, $P<0.02$), leading to an increased quality of life ($P<0.002$). One 47-year old patient, with very severe BPS/ICS since the age of 17, noted a relief of symptoms within 1-2 hours after the first injection, and reported a return to normal life. The patient with slowest onset reported improvement after one week of treatment. One patient reported a partial response. Nine of the patients reported a complete, or close to complete clinical response and these patients remain on Anakinra treatment and have been followed for a median of 428 days (range 80-706 days). One patient responded only transiently, and discontinued treatment after 80 days.

This clinical response was accompanied by a change in urine neuropeptide levels. The pain sensor SP is activated during acute cystitis[3] and inhibitors of the SP receptor NK1R reduce inflammation and pain in susceptible mice. SP levels were reduced in 9/10 patients during the first treatment round (FIG. 9). As treatment was interrupted, the resurgence of pain, frequency was accompanied by an increase in SP levels and when therapy was resumed, a return of pain relief and ease of micturition was accompanied by a reduction in SP levels.

To further understand the molecular basis of these effects, gene expression was analyzed longitudinally in RNA samples obtained; at onset, when the patients were in pain; at the time of maximum treatment effect in the first round; when pain returned during the treatment break; after reintroduction of Anakinra and at follow up, after 1-2 years of treatment. Gene expression, including canonical pathways involved in neuro-inflammation, TLR dependent pattern recognition and IL-1 signaling, was inhibited by treatment. Due to the pronounced effect on IL-1 related genes, we further investigated a gene network downstream of IL-1R1. In 8 out of 10 patients a marked reduction in IL-1R1 dependent gene expression was detected, primarily genes including CXCL1, IL1RAP CXCL3 and the IL1R1 gene itself.

By whole-exome sequencing, single nucleotide polymorphism (SNPs) were detected in IL-1-related genes including IL1A, IL1B, IL1RN, IL1R1, NLRP3, PYCARD, MMP7, TAC1 and TACR1. Allele frequencies in the patient group were compared to the NOMAD European database as well as allele frequencies at 1000 Genomes. Several SNPs were found in introns of these genes which included strong differences between the patients and the control populations for rs113540343 (IL1A), rs4251972 (IL1RN) and rs10754558 (NLRP3).

Several SNPs were identified in the IL1RN gene, which encodes the human IL-1 receptor antagonist after which Anakinra is designed. This suggests that the receptor antagonist might be defective in these patients, and hence the need for a correctly expressed IL-1 receptor antagonist in the form of anakinra. PYCARD encodes the inflammasome constituent ASC, which was identified as a cystitis susceptibility gene in mice. NLRP3 encodes the inflammasome component NLRP3 protein. Finally, SNPs were detected in TAC1 and TACR1, which encode the precursor of SP and its receptor NK1R, which drive pain sensing from the urinary bladder to dorsal root ganglia. The results suggest a genetic link between patients with bladder pain and IL-1 related genes that needs to be further evaluated in larger patient cohorts.

To further analyze the functional consequences of the SNPs we evaluated the effects of specific SNPs on experimentally determined 3-dimensional structures. Of the identified SNPs, rs145268073 and rs45507693 predict a change in the amino acid sequence of NLRP3 and IL1RN, respectively. In ILR1N, aa 99 was changed from an Alanine to a Threonine and in NLRP3, Arginine 488 was replaced by to a lysine or threonine. The atomic structures of both proteins have been solved individually and in complex with biologically binding partners (FIG. 11). The structure of ILR1N in complex with ILR1 (FIG. 11A, PDB ID: 1IRA) shows that the mutated A99 is situated in a central hydrophobic pocket with several relatively short non-polar contacts flanking the alanine's beta carbon (FIG. 11B). It is not unthinkable that the addition of a polar hydroxyl moiety might interfere sufficiently with this environment to indirectly alter the conformation of the nearby loop interfacing to ILR1.

In the complex structure of NLRP3 and activator, the mitotic NEK7 kinase, Arg488 is positioned in close proximity to key functional features of NLRP3 (FIG. 11C) (Sharif, H., et al. Structural mechanism for NEK7-licensed activation of NLRP3 inflammasome. *Nature* 570, 338-343 (2019). NLRP3 is found in an inactive conformation, but earlier studies of related NLRC4 shows that activation and inflammasome formation is likely accomplished through a 90 degree rigid body movement of the NBD-HB1 module relative to the remainder WHD-HD2-LRR module of NLRP3 (Zhang, L., et al. Cryo-EM structure of the activated NAIP2-NLRC4 inflammasome reveals nucleated polymerization. *Science* 350, 404-409 (2015)). The exact mechanisms that triggers this event are unknown, but it has been shown that ADP increases the stability of the NEK7/NLRP3 complex. R488, which reaches into the central pocket of WHD, has no apparent contacts to ADP and is seemingly not directly part of the interface between the WHD-HD2-LRR and NBD-HB1 modules but it is positioned at a junction central to NLRP3 inflammasome formation. It may be speculated that this residue may play a central role in the formation of active NLRP3, for which no structure yet is available.

TABLE 5

Patient characteristics

| ID | Age | M/F | Cath | Symptom Duration Year(s) | Inflammation Cytoscopy | Inflammation Histology | Concomitant disease | Other ongoing treatments |
|---|---|---|---|---|---|---|---|---|
| Bladder Pain Syndrome with mucosal inflammation (Hunner's Ulcer) | | | | | | | | |
| PI | 77 | F | Cath | 2 | Positive | Positive | Small contracted bladder, previous irradiation due to gynecological cancer, chronic obstructive pulmonary disease | Morphine |

TABLE 5-continued

Patient characteristics

| ID | Age | M/F | Cath | Symptom Duration Year(s) | Inflammation Cytoscopy | Inflammation Histology | Concomitant disease | Other ongoing treatments |
|---|---|---|---|---|---|---|---|---|
| PII | 67 | M | — | >10 | Positive | Positive | Gout | Allopurinol |
| PIII | 61 | M | CIC | 2 | Positive | Positive | Partial paraparesis, neurogenic bladder disorder, kidney stone | — |
| PIV | 67 | F | — | >10 | Positive | Positive | Arthrosis | — |
| PV | 67 | M | — | >2 | Positive | Positive | Gout | Allopurinol |
| PVI | 78 | F | — | 1 | Positive | Positive | Hydrothyroidosis | Levothyroxine |
| Bladder Pain Syndrome without mucosal inflammation | | | | | | | | |
| PVII | 47 | F | — | >10 | Negative | ND | Otherwise healthy | — |
| PVIII | 70 | M | — | <1 | Negative | ND | Prostate pain, Artrial fibrillation | — |
| PIX | 39 | F | — | 1 | Negative | ND | Otherwise healthy | — |
| PX | 70 | F | — | >10 | Negative | ND | Mb Dercum | — |

The invention claimed is:

1. A method for treating chronic inflammatory conditions in the lower urinary tract or for treating chronic pelvic pain syndrome, the method comprising administering to a subject in need thereof an effective amount of an IL-1 inhibitor.

2. A method according to claim 1 wherein the condition is chronic cystitis, chronic pelvic pain syndrome and/or bladder-associated pelvic pain.

3. A method according to claim 1 wherein the reagent is an interleukin-1 receptor antagonist.

4. A method according to claim 3 wherein the interleukin-1 receptor antagonist is an IL-1β inhibitor.

5. A method according to claim 3, wherein the interleukin-1 receptor antagonist is anakinra, or an active fragment or active variant thereof.

6. A method according to claim 1, wherein the subject has a variation in an IL-1 related gene.

7. A method of treating, alleviating or reducing pain and pain related symptoms of chronic pelvic pain syndrome, the method comprising administering to a subject in need thereof an effective amount of an IL-1 inhibitor.

8. The method according to claim 6, wherein the subject has a variation in one or more of IL1A, IL1B, IL1RN, IL1R1, NLRP3, PYCARD, MMP7, TAC1 and TACR1.

9. The method according to claim 8, wherein the subject has a variation in IL1A.

10. The method according to claim 8, wherein the subject has a variation in IL1B.

11. The method according to claim 8, wherein the subject has a variation in IL1RN.

12. The method according to claim 8, wherein the subject has a variation in NLRP3.

13. The method according to claim 8, wherein the subject has a variation at one or more of rs113540343 (IL1A), rs4251972 (IL1RN) and rs10754558 (NLRP3), rs145268073 (NLRP3), and rs45507693 (IL1RN).

14. The method according to claim 8, wherein the subject has a variation at rs113540343 (IL1A).

15. The method according to claim 13, wherein the subject has a variation at rs4251972 (IL1RN).

16. The method according to claim 13, wherein the subject has a variation at rs10754558 (NLRP3).

17. The method according to claim 13, wherein the subject has a variation at rs145268073 (NLRP3).

18. The method according to claim 13, wherein the subject has a variation at rs45507693 (IL1RN).

* * * * *